US006410724B1

(12) United States Patent
Dejean et al.

(10) Patent No.: US 6,410,724 B1
(45) Date of Patent: Jun. 25, 2002

(54) DIAGNOSTIC MEANS USEFUL FOR PREDICTIVE ASSESSMENT OF HUMAN HEPATOCELLULAR CARCINOMA DISEASE (HCC), AS WELL AS DIAGNOSTIC METHODS USING THE SAME

(75) Inventors: Anne Dejean, Paris; Marie-Annick Buendia, Le Perreux; Pascal Pineau, Paris, all of (FR); Hisaki Nagai, Kawasaki (JP); Pierre Tiollais, Paris (FR)

(73) Assignees: Institut Pasteur; Institut National de la Sante et de la Recherche Medicale (Inserm), both of Paris (FR)

( * ) Notice: Subject to any disclaimer, the term of this patent is extended or adjusted under 35 U.S.C. 154(b) by 0 days.

(21) Appl. No.: 09/402,453

(22) PCT Filed: Apr. 6, 1998

(86) PCT No.: PCT/IB98/00498

§ 371 (c)(1),
(2), (4) Date: Jan. 21, 2000

(87) PCT Pub. No.: WO98/45478

PCT Pub. Date: Oct. 15, 1998

Related U.S. Application Data

(60) Provisional application No. 60/043,437, filed on Apr. 7, 1997.

(51) Int. Cl.⁷ .............................. C07H 21/04; C12Q 1/68
(52) U.S. Cl. ................ 536/24.3; 536/24.31; 536/24.33; 536/23.1; 435/6
(58) Field of Search ............................. 536/23.1, 24.3, 536/24.33, 24.31; 435/6

(56) References Cited

PUBLICATIONS

Ahern, www.thescientist.library.upenn.edu/yr1995/july/tools_950724.htlm, Dec. 22, 1998.*

Verschuuren–Bemelmans et al. "Refinement by linkage analysis in two large families of the candidate region of the third locus (SCA3)" Human Genetics, vol. 96, p. 691–694, Dec. 1995.*

Stevanin et al. "The Gene for SCA3 is located in a region of about 3 cM" Am. J. Hum. Genet. vol. 56, p. 193–201, Jan. 1995.*

Sasaki et al. "Mappin gof the Gene for Machado–Joseph Disease within a 3.6–cM interval flanked by D14S291/D14S2809 and D14281" Am. J. Hum. Geneti. vol. 56, p. 231–242, Jan. 1995.*

Kuroki et al "Accumulation of Genetic Changes During Development and progression of HCC" Genes, Chromosomes, and Cancer, vol. 13, p. 163–167, 1995.*

Gyapay et al "the 1993–94 Genethon human genetic linkage map" Nature Genetics, vol. 7, pa 246–339, Jun. 1994.*

Matise et al "Automated construction of genetic linkage maps using an expert system" Nature Genetics, vol. 6, Apr. 1994.*

Yeh et al "Frequent genetic alterations at the distal region of chromosome 1q in HCC" Cancer Research, vol. 54, p. 4188–4192, Aug. 1994.*

Fujimori et al "Allelotype study of primary HCC" Cancer Research, vol. 51, p. 89–93, 1991.*

* cited by examiner

Primary Examiner—W. Gary Jones
Assistant Examiner—Jeanine Goldberg
(74) Attorney, Agent, or Firm—Oblon, Spivak, McClelland, Maier & Neustadt, P.C.

(57) ABSTRACT

The present invention pertains to new polynucleotides or new combinations of polynucleotides useful as diagnostic tools for predicting the occurrence of a human hepatocellular carcinoma disease. The invention is also directed to polynucleotides that consist in candidate tumor suppressor genes the alteration of which is involved in the occurrence of hepatocellular carcinoma in a patient, as well as to polynucleotides derived from such new candidate tumor suppressor genes and to the corresponding expressed polypeptides. The invention also concerns diagnostic methods using said polynucleotides as diagnostic tools.

5 Claims, 6 Drawing Sheets

Figure 1:
Figure 1:
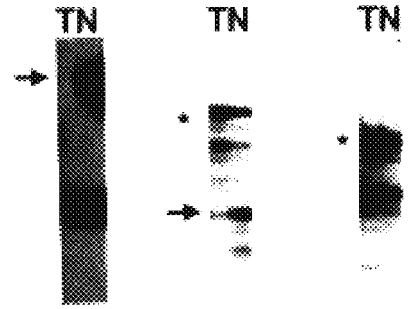
Figure 1:

DIAGNOSTIC MEANS USEFUL FOR PREDICTIVE ASSESSMENT OF HUMAN HEPATOCELLULAR CARCINOMA DISEASE (HCC), AS WELL AS DIAGNOSTIC METHODS USING THE SAME

This application is the National stage of PCT Application No. PCT/IB98/00498, filed Apr. 6, 1998 under 37 CFR 371. This application also claims priority to U.S. Provisional application No. 60/043,437, filed Apr. 7, 1997.

The present invention pertains to new polynucleotides or new combinations of polynucleotides useful as diagnostic tools for predicting the occurrence of a human hepatocellular carcinoma disease. The invention is also directed to polynucleotides that consist in candidate tumor suppressor genes the alteration of which is involved in the occurrence of hepatocellar carcinoma in a patient, as well as to polynucletides derived from such new candidate tumor suppressor genes and to the corresponding expressed polypeptides. The invention also concerns diagnostic methods using said polynucleotides as diagnostic tools.

Hepatocellular carcinoma (HCC) is the most common primary liver cancer in the world, with 251,000 new cases each year (Bosh et al., 1991) and, to date, this pathology carries a very poor prognosis. Epidemiological evidence has shown the predominant role of hepatitis B virus (HBV) as a major causal agent of liver cancer. Other risk factors include chronic infection with hepatitis C virus (HCV), alcohol abuse, environmental exposure to hepatocarcinogens such as aflatoxin B1, and several genetic diseases (Reviewed in Buendia et al., 1995, and described also in Bosch et al., 1991; Wogan, 1992). More particularly, epidemiologic studies indicate that more than 50% of HCCs are attributable to chronic hepatitis B virus (HBV) infection (Bosch et al., 1991). However, the role of hepatotropic viral agents and the molecular events leading to liver carcinogenesis remain unknown. A mutagenic role of HBV DNA integration in the host genome, that occurs frequently at early stages of HBV-associated tumorigenesis, was conclusively established only in rare cases (Dejean et al., 1986; De Thé et al., 1987; Wang et al., 1990), suggesting more indirect transformation pathways (Matsubara, 1991). Viral DNA integrated into hepatocyte DNA can be detected in about 80% of chronic HBV carriers (Chen et al., 1986).

A common feature in chronic viral hepatitis and liver cirrhosis is long lasting inflammation of the liver associated with chronic regenerative conditions, which might enhance the susceptibility of liver cells to genetic changes. HCC usually develops after a 20–50 year period of HBV chronic infection, often subsequent to cirrhosis (Lok et al., 1991). The long latent period before the establishment of carcinomas indicates that they are the result of a multistep process, and several studies have been directed toward the identification of common genetic alterations (Sugimura et al., 1992). Both activation of cellular oncogenes and inactivation of tumor suppressor genes have been implicated (Okuda et al., 1992; Sugimura et al., 1992).

Generally, the development of human cancer results from clonal expansion of genetically modified cells that acquired selective growth advantage through accumulated alterations of ptoto-oncogenes and tumor suppressor genes (Weinberg, 1991). Somatic inactivation of tumor suppressor genes is usually achieved by intragenic mutations in one allele of the gene and by the loss of a chromosomal region spanning the second allele.

The steps that lead to homozygosity of a mutant suppressor allele usually involve the flanking chromosomal regions as well. Accordingly, anonymous DNA markers mapping to nearby chromosomal sites, which may have shown heterozygosity prior to tumor progression, will suffer a parallel reduction to homozygosity (or loss of heterozygosity—LOH). Indeed the repeated observation of LOH of a specific chromosomal marker in cells from a particular type suggests the presence of a closely mapping tumor suppressor gene, the loss of which is involved in tumor pathogenesis (Hansen et al., 1987). The recessive action of mutant suppressor gene alleles permits any resulting phenotypic effects to be delayed for long periods of time after conception. These alleles are effectively latent until they are exposed by a reduction to homozygosity in one or another cell.

Thus, a tumor suppressor gene is a genetic element whose loss or inactivation allows a cell to display one or another phenotype of neoplastic growth deregulation. Such a definition exclude genes that are cytostatic or cytotoxic when introduced into a cell and inappropriately overexpressed. The arena of action of tumor suppressor genes may thus be defined: biochemically, these genes serve as transducers of anti-proliferative signals; biologically, they serve as part of the response machinery that enables a cell to stop progression through the cell cycle, to differentiate, to senesce, or to die (Weinberg, 1991).

Chromosomal analysis using polymorphic DNA markers that distinguish different alleles has revealed loss of hereozygosity (LOH) of specific chromosomal regions in various types of cancers and the mapping of regions with a high frequency of LOH has been critical for identifying negative regulators of tumor growth (Call et al., 1990; Fearon et al., 1990; Friend et al., 1986). The recent development of microstaellite polymorphic markers has allowed positional cloning of several tumor suppressor genes such as the BRCA1, BRCA2 and DPC4 genes (Hahn et al., 1996; Miki et al., 1994; Wooster et al., 1995).

Previous studies, mainly relying upon either restriction fragment length polymorphism (RFLP) markers or microsatellites markers restricted to specific chromosome arms, have defined a number of chromosomal regions of LOH in liver cancer. One of the most frequent allelic deletions in HCC has been found at chromosome 17p where the tumor suppressor gene p53 is located (Fujimori et al., 1991; Murakami et al., 1991; Slagle et al., 1991). The frequency of p53 mutations varies largely among HCC samples, depending on the geographic location in the world, and a hot spot mutation at codon 249 was observed in HCCs from regions with high levels of dietary aflatoxins and high prevalence of HBV infection (Bressac et al., 1991; Buetow et al., 1992; Hsu et al., 1991). Regional deletions spanning the RB locus on chromosome 13q have also been described, but in this case, a low mutation rate was found in the remaining allele (Murakami et al., 1991; Wang and Rogler, 1988; Zhang et al., 1994). The most frequent chromosome arm deletion is observed in 13q (53% of informative tumors). Deletions were encompassing a large region of 13q (13q12-q32) which harbors the RB and BRCA2 tumor suppressor genes (Friend et al., 1986; Wooster et al., 1995; Zhang et al., 1994). Other frequent LOH was reported on chromosome arms 1p, 4q, 5q, 6q, 8p, 10q, 11p, 16p, 16q and 22q (Buetow et al., 1989; De Souza et al., 1995; Emi et al., 1992; Fujimori et al., 1991; Takahashi et al., 1993, Tsuda et al., 1990; Wang and Rogler, 1988; Yeh et al., 1994). Candidate tumor suppressor genes in these regions include the mannose 6-phosphate/insulin-like growth factor II receptor gene (M6P/IGF2R) on 6q26-q27 (De Souza et al., 1995), the PDGF-receptor beta-like tumor suppressor gene (PRLTS) on 8p21-p22 (Fujiwara et al., 1995) and the E-Cadherin gene on 16q22 (Slagle et al., 1993).

Yeh et al. (1994) have performed a genetic analysis of HCC cell lines and 30 primary HCC tissues. Using 8 Polymorphic DNA markers for RFLP experiments and also microstaellites markers spanning 12 loci in chromosome 1p, these authors have shown that main chromosomal abnormalities seemed to cluster at the distal part of chromosome 1p, with a common region mapped to 1p35-36, which is also the region with frequent loss of heterozygosity in neuroblastoma and colorectal as well as breast cancers.

Tsuda et al. (1990) have studied allele loss on chromosme 16 by performing RFLP analysis of 70 surgically resected tumors by using 15 polymorphic DNA markers distributed overall both the short arm and the long arm of said chromosome. They detected LOH in 52% of informative cases (i.e. 36 cases), the common region of allele loss being located between the HP locus (16q22.1) and the CTRB locus (16q22.3-q23.2).

Fujimori et al. (1991) have realized an allelotype study of HCC by examining LOH with 44 RFLP markers in 46 cases of HCC. The markers used by Fujimori et al; represented all chromosomal arms excepted 5p, 8p, 9p, 18p and acrocentric chromosomes. Each chromosomal arm was thus mapped with only a single or two polymorphic RFLP markers. These authors have observed that a significant percentage of LOH occurred for chromosome arms 5q (4 deletions in 9 informative cases [44% LOH]), 10q (6 deletions in 24 informative cases[25% LOH]), 11p (6 deletions in 13 informative cases [46% LOH]), 16q (12 deletions in 33 informative cases[36% LOH]) and 17p (5 deletions in 11 informative cases [45% LOH]).

Buetow et al., (Buetow et al., 1989) reported LOH at the albumin gene locus (4q11-q12) in all of five informative HCCs, indicating that a tumor suppressor gene might lie in this region. The inventor's data suggest that alterations in two additional loci on chromosome 4q may play a role in liver carcinogenesis. Because chromosome 4q contains genes encoding growth factors or genes expressed predominantly in the liver such as albumin, alcohol dehydrogenase (ADH3), fibrinogen and UDP-glucuronyl-transferase, the deletion of this region might profoundly alter cell growth conditions and hepatocyte functions.

Buetow et al. (1989) have studied the LOH in 12 human primary liver tumors that have been tested against a panel of RFLP markers. These authors have typed tumor and non tumor issue for 11 RFLP markers spanning from 4q11-q13 to 4q32 chromosome 4 regions. In addition, Buetow et al. tested at least one RFLP marker on nine other chromosomes (1, 2, 6, 7, 9, 11, 13, 14 and 17) for allelic loss. The results showed that seven on nine tumors constitutionally heterozygous for chromosome 4q markers (six 4q RFLP markers were used by Buetow et al.) showed allele loss in tumor tissue. Six of the seven sample were jointly informative for both 4p and 4q markers (six 4p RFLP markers used). Among the other chromosomes informative for allele loss, one tumor showed changes in 13q. No other changes were observed in RFLP markers located on the eight other chromosomes tested. These authors concluded that a controlling locus involved in the pathogenesis of HCC might be in the vicinity of 4q32.

Emi et al. (1992) observed a frequent LOH for different loci on chromosome 8p in tumor tissues derived from HCC, colorectal cancer and lung cancer. More particularly, Emi et al. studied LOH in 120 HCC (46 of which had previously already been allelotyped by Fujimori et al. in 1991) tissues with five polymorphic markers along the short arm of chromosome 8 and defined commonly deleted regions within the same chromosomal interval, 8p23.1 to 8p21.3, suggesting that one or more tumor suppressor genes for HCC, and also for colorectal cancer, might be present in said region. The region of interest was mapped by Emi et al. using only three RFLP polymorphic DNA markers, respectively D8S238, MSR and D8S220. These authors concluded that a putative tumor suppressor gene might exist on 8p.

Becker et al. (1996), in order to investigate the chromosome 8 allele status in Chinese HCC, described that a panel of 37 matched normal and HCC DNAs from Qidong was analyzed for tumor specific allele loss with eight specific RFLP probes from both arms of chromosome 8. Tumor-specific LOH was found highest on the short arm with 71.4% (10/14) and 85% (17/20) of the informative patients missing an allele for 8p23 or 8p21 (only two RFLP specific probes used for the entire chromosome 8 short arm), respectively. Allele loss from the long arm of chromosome 8 was also observed with 30% (6/20) and 33.3% (7/21) of the samples informative for 8q22 and 8q24, respectively.

Boige et al., in 1996, have studied the allelic deletions in HCC, using 275 higly polymorphic microsatellites genetic markers spanning all non acrocentric chromosome arms in a group of 48 HCC. They observed that nine chromosome arms were deleted in more than 30% in 1p, 1q, 4q, 6q, 8p, 9p, 16p, 16q and 17p, the most frequent chromosome arm deletion being observed for 8p.

The scientific works described hereinbefore have allowed a primary but very coarse localization of the different genetic alterations occurring on the different chromosome arms present in the HCC tissue samples, due either to the weak number of genetic markers used and to the weak number of patients' tissue samples studied. The weak number of patients' tissue sample used in these studies did not provide conclusive or statistically significant data as to the frequence of a genetic alteration on a given chromosome arm or chromosome region. The poor precision with which the altered focuses were identified, and consequently the great size of the chromosome DNA fragments of interest that are bordered by the polymorphic DNA markers used in these studies, did not allow the one ordinary skill in the art to design and/or determine the suitable technical means useful to design accurate diagnostic tools for HCC, because none of the DNA fragments was shown in prior art to be sufficiently relevant and be considered as carrying the causal information for operating a precise correlation with the disease. Consequently, they did not permit the one ordinary skill in the art to clone specific DNA fragments from the chromosomes of healthy tissues, that were observed to be frequently altered during the occurrence of HCC.

Primary liver tumors, like other solid tumors in humans, most likely arise through a cascade of genetic events involving oncogenes and tumor suppressor genes that results in decreasing stability of the genome and ultimately leads to the malignant phenotype. The methods used according to the invention, that allowed an accurate and complete scan of 120 hepatocellular carcinoma genomes for allelic imbalance, are of decisive value for locating candidate genes implicated in liver cancer development.

The inventors have detected frequent changes in allelic dosage at particular regions of chromosomes 1p, 4q, 6q, 8p, 13q, 16p, 16q and 17p. In addition, the invention describes newly identified loci exhibiting a high rate of LOH on chromosome arms 1q, 2q, 9p, 9q, 14q and 17q. Genetic alterations of these regions have been observed in many other malignancies including breast cancers, small-cell lung carcinomas, prostate cancers, renal cell carcinomas, malignant melanomas or meningiomas, suggesting that tumor suppressor genes implicated in a wide spectrum of tumors may affect HCC progression (Cox et al., 1995; Hearly et al., 1995; Ranford et al., 1995; Takahashi et al., 1995; Takita et al., 1995).

The inventor's data indicate that a more telomeric locus than 8p21-p23, which shows a higher frequency of LOH compared to 8p21-p23 markers, is likely to contain a second candidate tumor suppressor gene for HCC. On the long arm of chromosome 4, the inventors have defined three non contiguous regions of LOH in 4q12, 4q22-q24 and 4q35. Chromosomal alterations at 4q are of great diagnostic value because they represent a preferential trait in HCC.

Further, the inventors have found frequent LOH with markers spanning a large region of 6q (Table 3 and data not shown).

The inventors have also found frequent LOH with markers depicted in Tables 2 and 4, therefore allowing the one skill in the art to determine the presence and characteristics of HCC-associated tumor suppressor genes existing on the different identified loci of interest, particularly on 8p21-8p23, 1p35-p36, 16q23-q24, 14q32, 4q and 6q.

Correlation of LOH with histological analysis of the adjacent non tumorous livers revealed that the frequency of deletions at combined chromosomal regions (1p, 6q, 8p and 13q) is significantly higher in HCCs arising on chronic hepatitis lesions than in HCCs developing on liver cirrhosis. It is here shown that when hepatocytes accumulate allelic changes under regenerative pressure, some combined chromosomal arm losses might constitute a "short-cut" towards malignancy.

The present inventors have now used a very dense panel of polymorphic microsatellite markers in order to precisely localize the different chromosomes regions being altered in HCC patients cancer liver tissue samples. The inventors have therefore performed a systematic screening of 120 HCC samples using 256 highly polymorphic microsatellite markers evenly distributed throughout non-acrocentric human autosomes. This is the first, large scale analysis of genomic alterations in human HCC using microsatellite markers. The data allow precise estimation of the relative frequency and accurate positioning of each chromosomal change.

The present invention thus concerns the use of DNA markers localized in specific chromosomal loci of interest (that are defined hereunder) as diagnostic tools allowing the prognosis of the hepatocellular carcinoma (HCC).

Because the inventors have now precisely identified the very small chromosomal regions that are subject to frequent genetic alterations, the DNA markers embraced by the present invention cover all the publicly available tools spanning these specific chromosomal loci of interest, namely:
1) Microsatellite DNA markers;
2) RFLP markers (usually constituted by specific oligonucleotide probes);
3) VNTR markers (Variable Number of Tandem Repeats), also named <<ministallites>> that are sequences of the <<Alu>> type of about twenty nucleotides that are repeated at high number of copies inside each VNTR, and which are detected either by a PCR reaction or a Southern blot hybridization;
4) STSs markers (Simple Tag Sequences), which are unique genomic sequences that can be amplified by a pair of specific oligonucleotide primers and which are generally non polymorphic;
5) ESTs (Expressed sequence Tags) which are transcribed in mRNA and that can be amplified by a pair of oligonucleotide primers.

The sequences of the DNA markers of the above groups 1) to 4) as well as the sequences of the oligonucleotide detection tools for each of them are freely publicly available on electronic databases, particularly on the Internet World Wide Web at the following address: <<http://www.ncbi.nlm.nih.gov)>>.

The present invention also concerns the use of polymorphic microsatellite DNA markers as diagnostic tools allowing the prognosis of the hepatocellular carcinoma (HCC).

The present invention is also directed to diagnostic methods using such microsatellite DNA markers, as well as to diagnostic kits comprising these polymorphic DNA markers and the reagents necessary to perform the diagnostic methods of the invention.

The present invention is further illustrated by the following Figures, without in anyway being limited in scope to the specific embodiments described in these Figures.

FIG. 1: Microsatellite analysis of primary HCCs for the presence of LOH. (A) Representative autoradiograms of allelic imbalance at different chromosomal loci showing allelic loss in tumors T53, T61, T32 and T48, concomitant gain and loss in tumor T58, and gain in intensity of one allele in tumor T20. (B) Representative informative (left) and non-informative cases (right) without LOH. Numbers at the top, microsatellites used. T and N, DNAs isolated from HCCs and adjacent non tumorous counterparts respectively. The sample numbers are listed below each autoradiogram. Arrows, alleles lost in the tumor sample. Asterisks denote increased signal intensity of one tumor allele.

Figure 2:
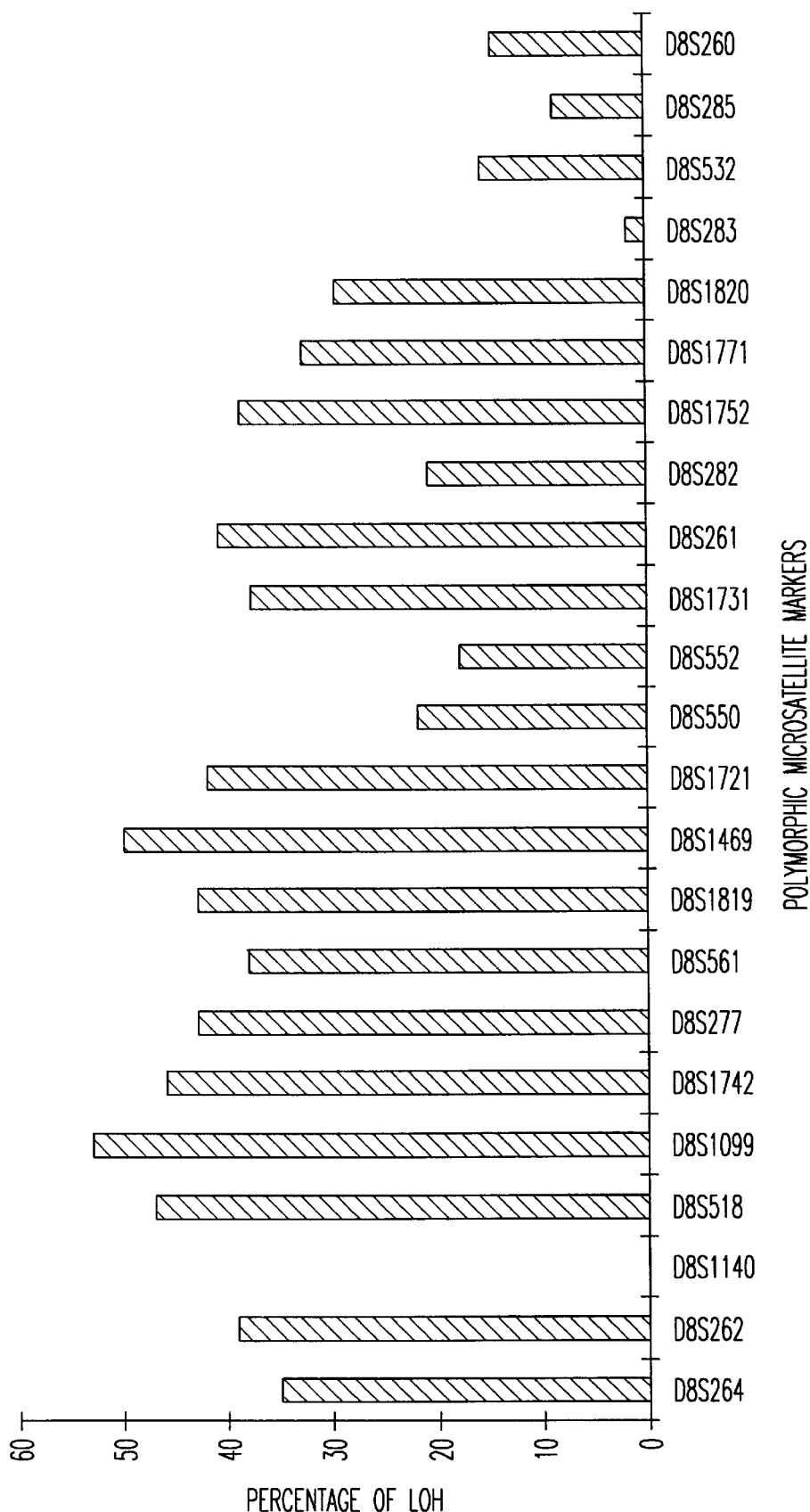

FIG. 2: Detailed analysis of microsatellite marker loci in the chromosome 8p region demonstrating significant percentage LOH in HCC allelotyping. Abscissa: Marker designation, the different markers being represented following their relative localization on chromosome 8p. Ordinate: Percentage of allelic imbalance (LOH/informative cases× 100).

Figure 3:
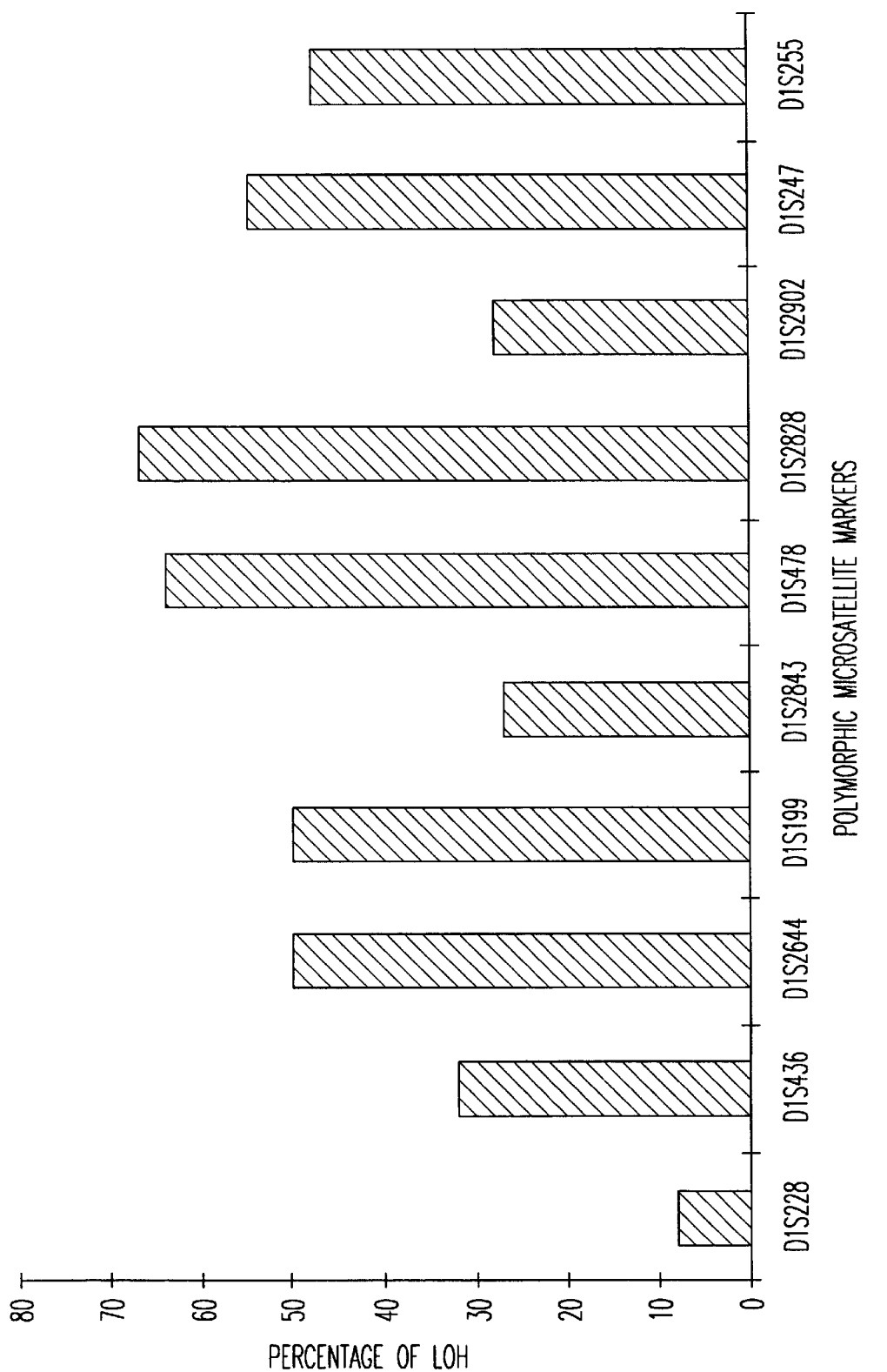

FIG. 3: Detailed analysis of microsatellite marker loci in the chromosome 1p35-p36 region demonstrating significant percentage LOH in HCC allelotyping. Abscissa: Marker designation, the different markers being represented following their relative localization on chromosome 1p. Ordinate: Percentage of allelic imbalance (LOH/informative cases× 100).

Figure 4:
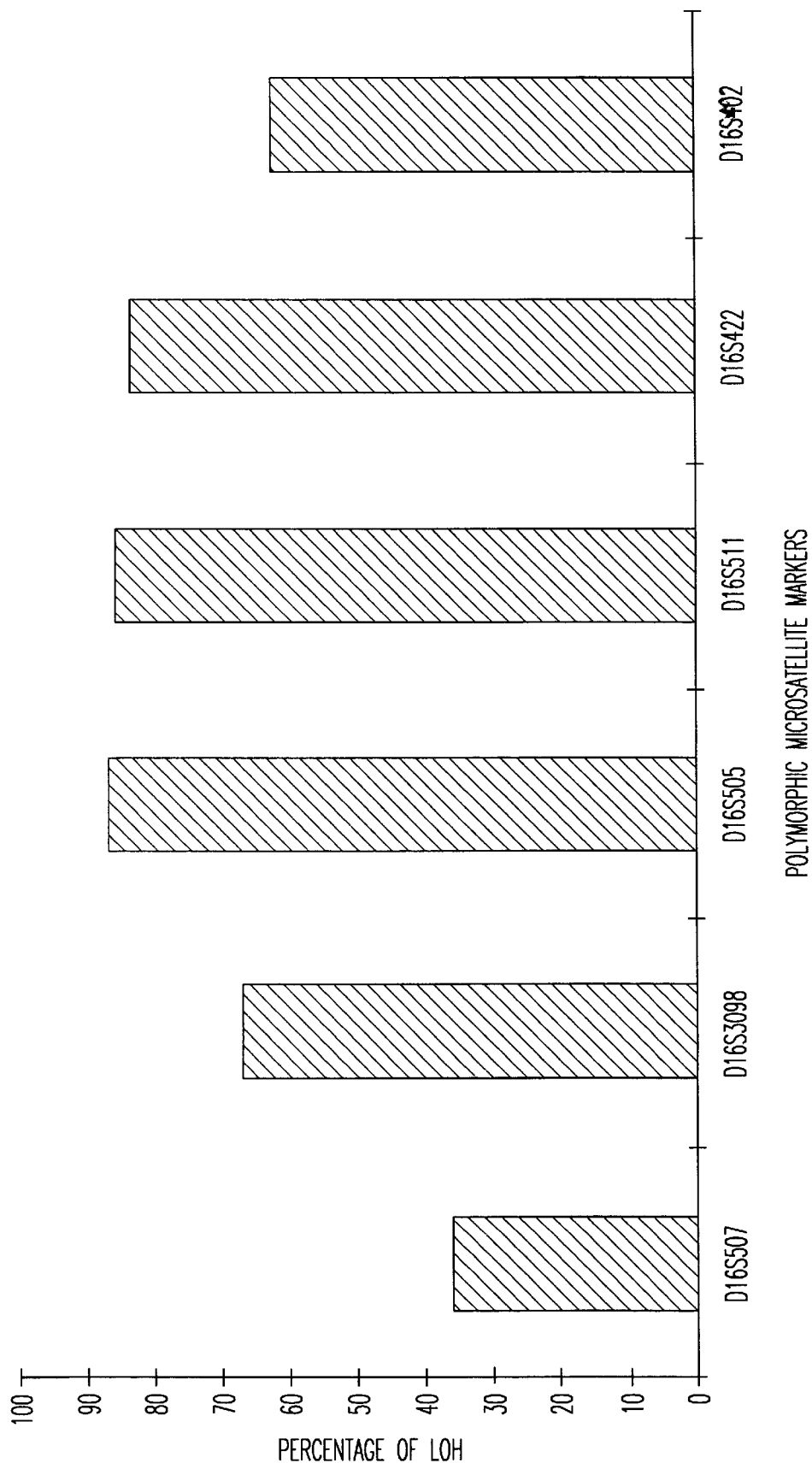

FIG. 4: Detailed analysis of microsatellite marker loci in the chromosome 16q23-q24 region demonstrating significant percentage LOH in HCC allelotyping. Abscissa: Marker designation, the different markers being represented following their relative localization on chromosome 16q. Ordinate: Percentage of allelic imbalance (LOH/informative cases×100).

Figure 5:
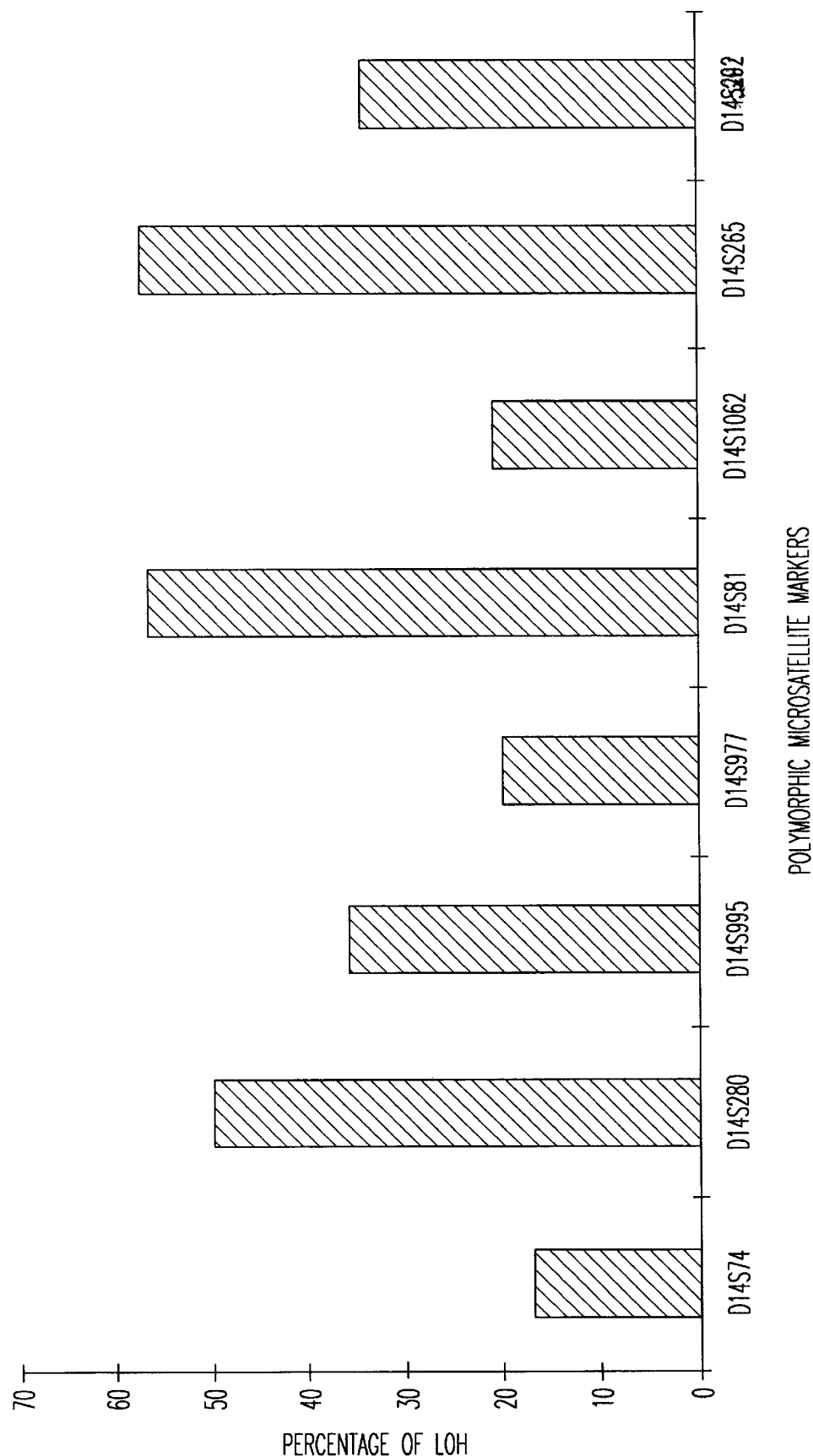

FIG. 5: Detailed analysis of microsatellite marker loci in the chromosome 14q32 region demonstrating significant percentage LOH in HCC allelotyping. Abscissa: Marker designation, the different markers being represented following their relative localization on chromosome 14q. Ordinate: Percentage of allelic imbalance (LOH/informative cases× 100).

Figure 6:
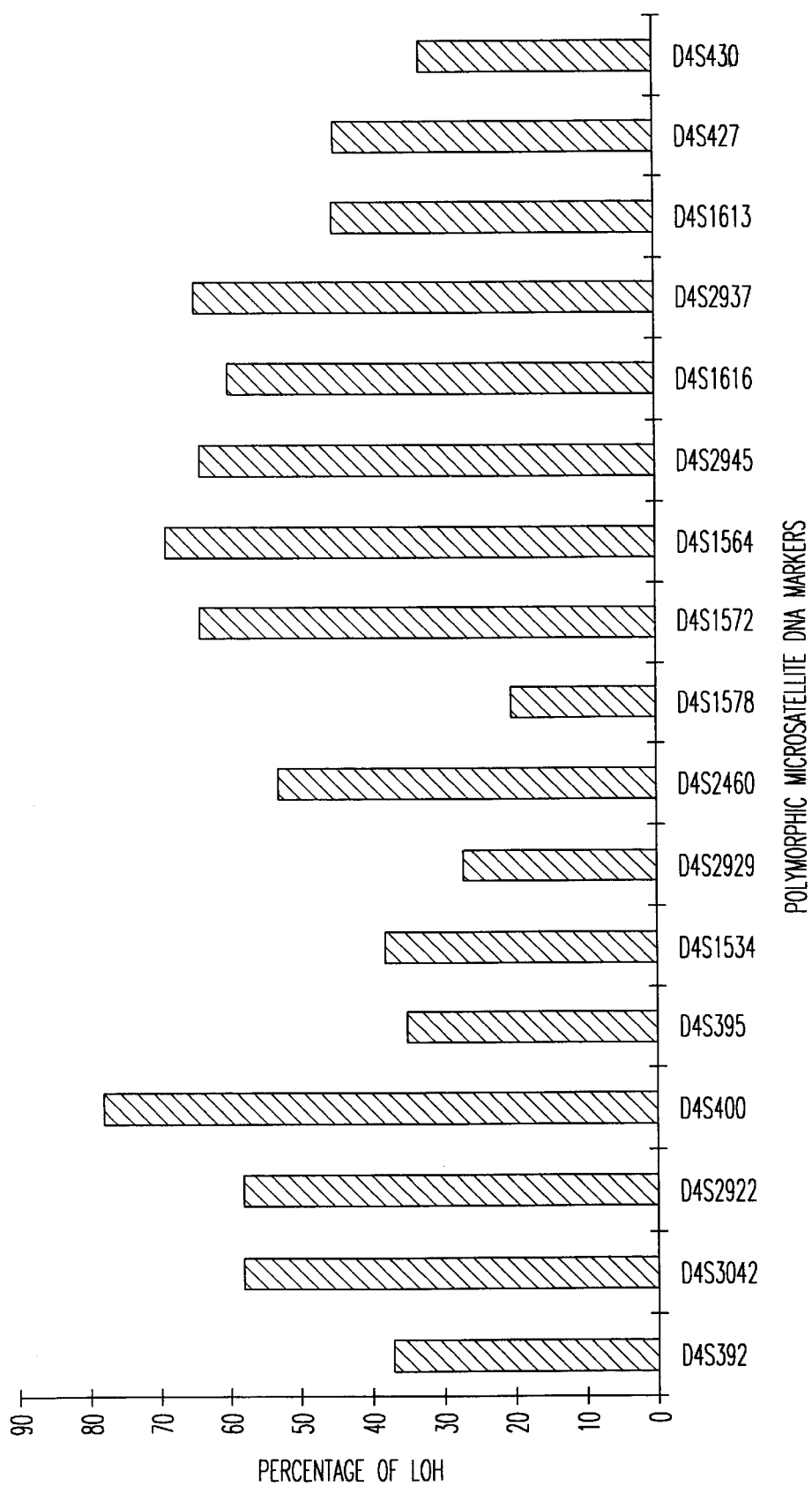

FIG. 6: Detailed analysis of microsatellite marker loci in die chromosome 4q35-q36 region demonstrating significant percentage LOH in HCC allelotyping. Abscissa: Marker designation, the different markers being represented following their relative localization on chromosome 4q. Ordinate: Percentage of allelic imbalance (LOH/informative cases× 100).

As already mentioned above, the fact that the inventors have now precisely identified the very small chromosomal regions that are subject to frequent genetic alterations allow the one ordinary skill in the art to use any publicly available DNA markers contained in the art that detect a specific chromosomal locus o interest according to the present invention to perform a diagnostic method of the invention or to clone tumor suppressor genes in the corresponding chromosomal regions of interest. More particularly, the DNA markers embraced by the present invention cover all the publicly available tools spanning these specific chromosomal loci of interest, namely:

1) Microsatellite DNA markers;
2) RFLP markers (usually constituted by specific oligonucleotide probes);
3) VNTR markers (Variable Number of Tandem Repeats), also named <<ministallites>> that are sequences of the <<Alu>> type of about twenty nucleotides that are repeated at high number of copies inside each VNTR, and which are detected either by a PCR reaction or a Southern blot hybridization;
4) STSs markers (Simple Tag Sequences), which are unique genomic sequences that can be amplified by a pair of specific oligonucleotide primers and which are generally non polymorphic;
5) ESTs (Expressed sequence Tags) which are transcribed in mRNA and that can be amplified by a pair of oligonucleotide primers.

The sequences of the DNA markers of the above groups 1) to 4) as well as the sequences of the oligonucleotide detection tools for each of them are freely publicly available on electronic databases, particularly on the Internet World Wide Web at the following address: <<http:H/www.ncbi.nlm.nih.gov>>.

An object of the present invention consists in a composition for the predictive diagnosis of an hepatocellular carcinoma in a patient comprising at least a polynucleotide containing a DNA marker which is localized in the following chromosomal regions:

a) 1p;
b) 1q;
c) 2q;
d) 4q;
e) 6p;
f) 7p;
g) 7q;
h) 8p;
i) 8q;
j) 9p;
k) 9q;
l) 10q;
m) 13q;
n) 14q;
o) 16p;
p) 16q;
q) 17p;
r) 17q.

said DNA markers being any of the publicly available markers spanning these specific chromosomal loci of interest, namely:
1) Microsatellite DNA markers;
2) RFLP markers;
3) VNTR markers (Variable Number of Tandem Repeats);
4) STSs markers (Simple Tag Sequences);
5) ESTs (Expressed sequence Tags).

Another object of the present invention consists in a composition for the predictive diagnosis of an hepatocellular carcinoma in a patient comprising at least one polynucleotide containing a DNA marker which is localized preferably in the following chromosomal regions:

a) 8p23;
b) 8p122;
c) 8p21;
d) 1p35-p36;
e) 16q23-q24,
f) 14q32 and
g) 4q35-q36, said DNA markers any of the publicly available markers spanning these specific chromosomal loci of interest, namely, microsatellite DNA markers, namely:
1) Microsatellite DNA markers;
2) RFLP markers;
3) VNTR markers (Variable Number of Tandem Repeats);
4) STSs markers (Simple Tag Sequences);
5) ESTs (Expressed sequence Tags).

The present invention thus concerns the use of polymorphic microsatellite DNA markers as diagnostic tools allowing the prognosis of the hepatocellular carcinoma (HCC).

A summary of the different loci localization using microsatellite DNA markers in each chromosome pair in human has been described by Dib C. et al. in 1996. The full sequences of the whole microsatelites DNA markers as well as the full sequences of the amplicons generated using these microsatellite DNA markers are freely publicly available on electronic databases (Genbank, STS Bank), more particularly on the Internet World Wide Web at the following address: <<http://www.genethon.fr>>

The present invention is also directed to diagnostic methods using such microsatellite DNA markers, as well as to diagnostic kits comprising these polymorphic DNA markers and the reagents necessary to perform the diagnostic methods of the invention.

As already discussed hereinbefore, the DNA fragments that are frequently altered during HCC are strongly thought to carry tumor suppressor genes that are no longer expressed when they are altered in the cancerous tissues. Due to the precision of the new chromosome mapping realized herein by the inventors, it is now possible to achieve the cloning of the wild DNA fragments corresponding to the altered chromosome regions found in HCC tissue samples in order to characterize and sequence the candidate tumor suppressor genes carried by these DNA fragments and subsequently expect the use of these cloned genes of interest in the field of diagnostic and also in the area of therapeutics, specifically for gene therapy.

Each of the polymorphic microsatellite DNA markers used according to the present invention consists in a pair of specific primers having a sequence that is complementary to a genomic DNA sequence flanking respectively the 5' end and the 3' end of a higly polymorphic microstaellite genomic DNA segment constituted by a polymer of Cytidine-Adenine (5'- . . . CACA . . . -3') sequence of a known length. A polymorphic microsatellite DNA marker is used to amplify the microsatellite DNA segment which is then identified by its specific length, for example in a polyacrylamide gel electrophoresis in the presence of urea, as described in the Materials and Methods Section.

The preferred polymorphic microsatellite DNA markers used in the diagnostic methods and kits according to the present invention, as well as for cloning the tumor suppressor gene carried by the DNA fragments of interest according to the present invention are depicted in Tables 1, 2 and 4.

In a specific embodiment of the invention, the poly DNA markers that are preferably used in the diagnostic and cloning methods according to the invention are those that specifically hybridize with chromosomal regions that undergo frequent alterations, i.e. the chromosomal regions for which the percentage of LOH has been found by the inventors to be higher than 20%.

More preferably, the specific polymorphic markers used in the diagnostic and cloning methods according to the invention are those for which the LOH percentage is higher than 30%, and most preferably those for which the LOH percentage is larger than 35%.

In Tables 2 and 4 are represented a summary of microsatellite marker loci undergoing significant percentage of LOH.

The microsatellite DNA markers names used according to the present invention are the scientific conventional names for which, notably, the Genethon organism (Evry, France) has defined specific pairs of primers permitting to amplify them, each of the said primers being also useful as a specific probe for detecting the corresponding microsatellite DNA marker.

The invention concerns a composition for the predictive diagnosis of an hepatocellular carcinoma comprising at least one polynucleotide of the two nucleic acid molecules constituting the pair of primers of at least one microsatellite DNA marker choosen among the following microsatellite DNA markers:
a) 1p: D1S243, D1S214, D1S228, D1S199, D1S255, D1S476, D1S198, D1S207, D1S248, D1S436, D1S2644, D1S2843, D1S478, D1S2828, D1S2902, D1S247 and D1S255;
b) 1q: D1S305, D1S196, D1S238, D1S249, D1S229, D1S235 and D1S304;
c) 2q: D2S113, D2S347, D2S151, D2S294, D2S311, D2S143, D2S159, D2S336 and D2S125;
d) 4q: D4S392, D4S1538, D4S1578, D4S406, D4S430, D4S422, D4S1548, D4S1597, D4S408, D4S426, D4S3042, D4S2922, D4S400, D4S395, D4S1534, D4S2929, D4S2460, D4S1572, D4S1564, D4S2945, D4S1616, D4S2937, D4S1613 and D4S427;
e) 6p: D6S344, D6S305, D6S260, D6S276, D6S426 and D6S294;
f) 7p: D7S531, D7S664, D7S493, D7S484 and D7S519;
g) 7q: D7S669, D7S657, D7S486, D7S495, D7S483 and D7S550;
h) 8p: D8S277, D8S550, D8S282, D8S283 and D8S260, D8S264, D8S262, D8S1140, D8S518, D8S1099, D8S1742, D8S561, D8S1819, D8S1469, D8S1721, D8S552, D8S1731, D8S261, D8S1752, D8S1771, D8S1820, D8S532 and D8S285;
i) 8q: D8S273, D8S281, D8S263 and D8S272;
j) 9p: D9S288, D9S156, D9S161 and D9S273;
k) 9q: D9S153, D9S277, D9S195, D9S164 and D9S158;
l) 10q: D10S589, D10S185, D10S597, D10S587 and D10S212;
m) 13q: D13S175, D13S171, D13S284, D13S170, D13S158, D13S285 and D13S286;
n) 14q: D14S261, D14S75, D14S63, D14S74, D14S292, D14S81, D14S280, D14S995, D14S977, D14S1062 and D14S265;
o) 16p: D16S521, D16S407, D16S420 and D16S411;
p) 16q D16S408, D16S518, D16S422 and D16S520, D16S507, D16S3098, D16S505, D16S511, D16S422 and D16S402;
q) 17p: D17S926, D17S786 and D17S953;
r) 17q: D17S933, D17S787, D17S949, D17S784 and D17S928;

The diagnostic composition according to the invention comprises preferably at least two polynucleotides choosen among the nucleic acid molecules constituting the pair of primers of a microsatelllite DNA markers of groups a) to r), providing that said polynucleotides do not belong to the same pair of primers defining said DNA marker.

Among the markers depicted in Table 2, the most preferred markers used according to the present invention are the followings: D4S426 (4q35; 40% LOH), D6S305 (6q27; 36% LOH), D7S493 (7p15; 30% LOH), D8S277 (8p23; 42% LOH), D13S284 (13q14; 30% LOH), D17S786 (17p13; 33% LOH).

As the inventors have also detected significant LOH percentage in loci that had never been associated with the occurrence of HCC before the date of the invention, other preferred polymorphic DNA markers used according to the present invention are also the followings: D1S238 (1q22-q23; 20% LOH), D1S235 (1q42-q43; 24% LOH), D2S336 (2q36-q37; 29% LOH), D2S125 (2q36-q37; 20% LOH), D7S495 (7q33-q34; 20% LOH), D8S263 (8q23-q24; 23% LOH), D9S273 (9p12-p14; 21% LOH), D9S164 (9q34-qter; 20% LOH), D14S81 (14q32; 23% LOH) and d17S928 (17q24-qter; 21% LOH).

Furthermore, the inventors have more precisely defined four chromosomal regions using polymorphic markers that are distant one to each other of less than 0.25–1 centimorgan (cM) on the genetic map. These very precise mappings are shown in FIGS. 2 to 5 for the following chromosomal regions:
a) chromosomal 8p region (FIG. 2 and Table 4);
b) chromosomal 1p35-36 region (FIG. 3 and Table 4);
c) chromosomal 14q32 region (FIG. 4 and Table 4);
d) chromosomal 16q23-q24 region (FIG. 5 and Table 4);
e) chromosomal 4q35-q36 region (FIG. 6 and Table 4).

For the purpose of the present invention, the following 8p markers are useful: D8S264, D8S262, D8S518, D8S1742, D8S277, D8S1819, D8S1721, D8S 1731, D8S1752.

For the chromosomal 8p region (see also FIG. 2), the inventors have now detected at least four regions for which is observed a very high percentage of LOH.

The first peak of LOH is seen in 8p23 using the D8S1742 polymorphic marker (53% LOH in 54 informative cases). The region comprised between marker D8S262 and D8S1819 (about 2 cM in length) is more likely to harbor a tumor suppressor gene. This specific region is thus a more preferred region according to the present invention. The second peak of LOH is seen in 8p22 using the D8S1469 polymorphic marker (50% LOH in 40 informative cases). The third peak of LOH is seen using the D8S1731 polymorphic marker (38% LOH in 52 informative cases). Finally, the fourth peak of LOH is seen using the D8S1752 polymorphic marker (39% LOH in 62 informative cases).

Consequently, the following polymorphic DNA markers D8S1742, D8S1469, D8S1731 and D8S1752 are also among the preferred markers used in the diagnostic and cloning methods according to the present invention.

For the purpose of the present invention, the following 8p markers are useful: D1S436, D1S2644, D1S199, D1S478, D1S2828, D1S247 and D1S255.

For the chromosomal 1p35-p36 region (see also FIG. 3), the inventors have now detected at least six regions for which is observed a very high percentage of LOH The first peak of LOH is seen using the D1S2644 polymorphic marker (50% LOH in 30 informative cases). The second peak of LOH is seen using the D1S199 polymorphic marker (50% LOH in 50 informative cases). The third peak of LOH is seen using the polymorphic marker D1S478 polymorphic marker (64% LOH in 28 informative cases). The fourth peak of LOH is seen using the D1S2828 polymorphic marker (67% LOH in 9 informative cases). The fifth peak of LOH is seen using the D1S247 polymorphic marker (55% LOH in 31 informative cases). The sixth peak of LOH is seen using the D1S255 polymorphic marker (48% LOH in 50 informative cases).

Consequently, the following polymorphic DNA markers D1S2644, D1S199, D1S478, D1S2828, D1S247 and D1S255 are aslo among the preferred markers used in the diagnostic and cloning methods according to the present invention.

For the chromosomal 14q32 region (see also FIG. 4), the inventors have now detected at least five regions for which is observed a very high percentage of LOH.

The first peak of LOH is seen using the D14S280 polymorphic marker (50% LOH in 10 informative cases). The second peak of LOH is seen using the D14S995 polymorphic marker (36% LOH in 14 informative cases). The third peak of LOH is seen using the polymorphic marker D14S81 (57% LOH in 28 informative cases). The fourth peak of LOH is seen using the polymorphic marker D14S265 (58% LOH in 12 informative cases). The fifth peak of LOH is seen using the polymorphic marker D14S292 (35% LOH in 17 informative cases).

Consequently, the following polymorphic DNA markers D14S280, D14S995, D14S81, D14S265 and D14S292 are aslo among the preferred markers used in the diagnostic and cloning methods according to the present invention.

For the 16q23-q24 chromosomal region (see also FIG. 5), the inventors have now detected at least five regions for which is observed a very high percentage of LOH The first peak of LOH is seen unsing the D16S3098 polymorphic marker (67% LOH in 15 informative cases). The second peak of LOH is seen using the D16S505 polymorphic marker (87% LOH in 15 informative cases). The third peak of LOH is seen using the D16S511 polymorphic marker (86% LOH in 14 informative cases). The fourth peak of LOH is seen using the D16S422 polymorphic marker (84% LOH in 25 informative cases). The fifth peak of LOH is seen using the D16S402 polymorphic marker (63% LOH in 19 informative cases).

Consequently, the following polymorphic DNA markers D16S3098, D16S505, D16S511, D16S422 and D16S402 are aslo among the preferred markers used in the diagnostic and cloning methods according to the present invention.

For the 4q35-q36 chromosomal region (See also FIG. 6), the inventors hace now detected several regions for which is observed a very high percentage of LOH.

The first peak of LOH is seen unsing the D4S400 polymorphic DNA marker (78% LOH in 9 informative cases). A large region has been determined to undergo frequent LOH occurrences, said region being physically comprised between the D4S1572 and the D4S2937 polymorphic DNA marker.

Consequently, the following polymorphic DNA markers D4S400, D4S1572, D4S1564, D4S2945, D4S1616 and D4S2937 are aslo among the preferred markers used in the diagnostic and cloning methods according to the present invention In one preferred embodiment of the diagnostic methods and diagnostic kits according to the present invention, these methods and kits comprise a combination of at least two of the polymorphic DNA markers of Table 2 or Table 4, preferably a combination of a number of said polymorphic markers ranging from two to ten polymorphic markers, more preferably a number ranging from two to five polymorphic markers and most preferably a number ranging from two to four polymorphic markers and ideally three polymorphic DNA markers.

Preferably, the combination of the polymorphic markers used according to the present invention is choosen in such a manner that they are selected among the markers for which the highest LOH percentage in HCC has been found by the inventors.

In a preferred embodiment of the combinations of the microstaellite markers according to the present invention, each combination comprise at least one marker for each of the chromosomal regions depicted in Tables 2 and 3.

More preferably, each combination of microsatellite DNA markers comprise at least one DNA marker for each chromosmal region depicted in Table 4, thus for each of the following chromosomal regions: 8p, 1p35-p36, 16q23-q24, 4q35-q36 and 14q32. More specifically the combinations preferably comprise at least one marker for each of the following 8p sub-regions: 8p23, 8p22 and 8p21.

The most preferred combinations of microsatellite DNA markers comprise at least one DNA marker choosen in each of the following groups 1) to 4):
1) 8p: D8S264, D8S262, D8S518, D8S1742, D8S277, D8S1819, D8S1721, D8S1731, D8S1752;
2) 1p35-p36: D1S436, D1S2644, D1S199, D1S478, D1S2828, D1S247 and D1S255;
3) 16q23-q24: D16S3098, D16S505, D16S511, D16S422 and D16S402;
4) 14q32: D14S280, D14S81 and D14S265;
5) 4q35-q36: D4S400, D4S1572, D4S1564, D4S2945, D4S1616 and D4S2937.

Thus, another object of the present invention consists in diagnostic methods and diagnostic compositions using or comprising the above described combinations of microstallite polymorphic DNA markers.

In one preferred embodiment of the diagnostic compositions comprising the above described combinations of DNA markers, a single DNA marker is choosen in each group.

The invention also concerns diagnostic kits comprising the diagnostic compositions according to the invention as well as the suitable reagents necessary in order to perform the diagnostic tests.

The results described herein have allowed the inventors to discover that correlations occur between specific alterations in different chromosomal loci amplified with the polymorphic DNA markers used according to the present invention in case of HCC. More precisely, the inventors have observed that the frequency of LOH identified concomitantly on both arms 1p and 13q, 1p and 8p as well as 6q and 13q are significantly higher in tumors arising from chronic hepatitis lesions (CH) than liver cirrhosis (LC), the numbers of HCCs with CH vs. LC showing LOH in the above combinations being 15 vs.5, 16 vs. 6, and 14 vs. 3 respectively.

Consequently, diagnostic compositions comprising a specific combination of markers for which a correlation of LOH have been determined are useful in order to help the practitioner to discriminate between HCCs with liver cirrhosis and HCCs with chronic hepatitis lesions.

Thus, in one specific embodiment of the diagnostic methods and diagnostic compositions according to the present invention that are useful to discriminate between HCCs with liver cirrhosis and HCCs with chronic hepatitis lesions, the polymorphic DNA markers are preferably used in combination.

For the purpose of this specific embodiment, the invention is also directed to diagnostic compositions comprising at least one DNA marker choosen in each of the following groups a) to c):
a) markers of 1p, choosen among D1S243, D1S214, D1S228, D1S199, D1S255, D1S476, D1S198, D1S207 and D1S248, with markers of 13q, choosen among D13S175, D13S171, D13S284, D13S170, D13S158, D13S285 and D13S286;

b) markers of 1p, choosen among D1S243, D1S214, D1S228, D1S199, D1S2155, D1S476, D1S198, D1S207 and D1S248 with markers of 8p, choosen among D8S264, D8S262, D8S518, D8S1742, D8S277, D8S1819, D8S1721, D8S1731, D8S1752;

c) markers of 6q, choosen among D6S462, D6S261, D6S292, D6S290, D6S305, D6S446 and D6S281 with markers of 13q, choosen among D13S175, D13S171, D13S284, D13S170, D13S158, D13S285 and D13S286.

The inventors have also discovered that a frequent LOH on 1p and 1q occurred in small HCCs classified as T1 although in the same early tumors few changes are noted on 2q, 6q, 7q, 8q, 14q, 16pq and 17pq (0–1 of 10 tumors).

On another hand, the inventors have discovered that the allelic imbalance on 16p and 17p appears frequently in invasive tumors having intrahepatic metastasis or portal vein invasions compared to non-invasive tumors.

These observations have led the inventors to design specific embodiments of the diagnostic methods and kits according to the present invention in order to provide useful diagnostic tools permitting the typing of a HCC tumor as an early or an invasive tumor state. In this specific embodiment of the diagnostic methods and kits according to the present invention, specific combinations of the polymorphic DNA markers of Tables 1 and 2 are used, in order to discriminate between genetic alterations occurring preferentially in early tumors and genetic alterations occurring preferentially in invasive cancer states.

Thus, are also part of the present invention diagnostic compositions comprising a combination of microsatellite DNA markers, each combination containing at least one DNA marker choosen in every following groups:

a) Microstallite markers of 16p, choosen among D16S521, D16S407, D16S420 and D16S411;

b) Microsatellite markers of 17p, choosen among D17S926, D17S786, and D17S953, it being understood that the occurrence of LOH using the above diagnostic compositions are useful to diagnose invasive tumors and that the absence of LOH using these diagnostic compositions will mean a strong support for either early tumors diagnosis or the absence of an HCC.

The present invention pertains also to diagnostic methods, to detect a HCC or a HCC predisposition in a patient, using the markers [(1) Microsatellite DNA markers; 2) RFLP markers; 3)VNTR markers (Variable Number of Tandem Repeats); 4) STSs markers (Simple Tag Sequences); 5) ESTs (Expressed sequence Tags)] localized in the loci of interest defined by the inventors. More particularly, the diagnostic methods according to the present invention are using the microsatellite markers of Tables 2 and 4 as well as the diagnostic compositions according to the invention that are described above.

Such diagnostic methods embrace all methods that permit the detection of an allelic alteration in the chromosome loci of interest.

A preferred diagnostic method according to the present invention is a method allowing the detection of a loss of heterozigosity (LOH) at a particular locus amplified with the help of one DNA marker used herein or at several specific loci amplified with the help of a combination of at least two microsatellite DNA markers, specifically a combination contained in the diagnostic compositions according to the present invention.

Such a diagnostic method permitting the dectection of LOH comprises the following steps:

a) Preparing two tissue samples from a patient, the first tissue sample being derived from an organ different than the liver and the second tissue sample being derived from the liver of said patient;

b) Making the genomic DNA contained in the cells of the tissue samples of step a) available to hybridization;

c) Amplifying the genomic DNA of step b) with at least one microsatellite DNA marker choosen among the markers depicted in Tables 2 and 4 or a composition containing a combination of DNA markers according to the present invention;

d) detecting the alterations that have occurred by comparing the resulting amplified products of step c) derived respectively from the first and the second tissue sample.

The details for the amplification and detection steps of one preferred embodiment of the above diagnostic method are fully described in the Materials and Methods section.

In a preferred embodiment of the above described diagnostic method according to the invention, step d) is making use of at least one of the primers constituting the amplifying tools of step c) as oligonucleotide probes (detection tools), said probes being preferentially radioactively or non-radioactively labelled.

The discovery of the inventors that specific small chromosomal regions are now mapped for frequent genetic alteration during an HCC is allowing the one skill in the art to identify and clone the tumor suppressor genes that have been altered in case of an HCC.

The inventors have now precisely mapped the chromosomal regions undergoing frequent genetic alterations, specifically allelic imbalance, the distance between the different DNA markers used being from 2 centimorgans (cM) for the markers the most distant one from each other and being less than 0.25 cM for the markers that are the less distant one form each other, it being generally accepted that 1 cM represents approximately 1000 kilobases +/−20%. Thus, for the nearest markers, specifically in the 8p region, they are distant on the genome of less than 0.25 cM, or in other words they are distant of less than 250 kilobases, and sometimes less than about 100 kb, specially for the microsatellite markers localized in 8p21, 8p22 and 8p23.

In order to isolate candidate tumor suppressor genes localized between the chromosomal positions of two DNA markers according to the present invention, it is first proceeded with the isolation of at least one yeast artificial chromosome (YAC) clone which are known to span the genomic DNA between the loci of interest. The YAC libraries are publicly available in Genethon (Evry, France). For the 8p region, the following YACs are used: 852d10 (spanning a chromosomal region containing at least from D8S518 to AFM249WA9 microstallite DNA markers localizations), 787c11 (from D8S264 to WI-9756), 842b11 (from D8S518 to to AFM249WA9), 745a3 (from AFMB322ZH9 to AFM249WA9), 832g12 (from AFMB322ZH9 to WI-9756), 807a1 (from D8S518 to AFM249WA9), 765c4 (from D8S518 to AFM249WA9), 920h7 (from D8S518 to AFM249WA9), 764c7 (from WI-3823 to D8S1706), 792a6 (from D8S277 to WI-8327), 879f11 (from D8S561 to WI-8327), 910d3 (from D8S561 to D8S1819), 910f12 (from D8S561 to WI-3823), 967c11 (from D8S277 to WI-8327), 918c6 (from D8S561 to D8S1819) and 856d8 (from D8S561 to D8S1819).

The markers hereinabove mentioned are comprised among the following microsatellite DNA markers arranged in the 8p region, from 8p23 to 8p21, in the following order: NIB9, WI-6641, WI-4250, D8S504, WI-5411, XI-1986, D8S264, D8S262, D8S1824, D8S201, AFMB322ZH9, D8S518, WI-9756, AFM249WA9, D8S561, D8S277, WI-3823, D8S1819, D8S1706 and WI-8327.

As an illustrative example of the cloning method of a candidate tumor suppressor gene contained in a region of interest determined according to the present invention, it will be given the cloning method of a candidate tumor suppressor gene localized in the 8p23 region.

Cosmid libraries are constructed from the YAC clone spanning the 8p23 genomic DNA. For example, the cosmid library is constructed following the technique described by Shimizu et al. in 1990. Briefly, the cosmid vector pWEX15 (Wahl et al., 1987), whose unique BamHI site is filled by Klenow enzyme and converted into a unique XhoI site using an oligonucleotide linker (5'CCTCGCGAGG-3'). pWEX15 is then digested with XhoI and partially filled in with dCTP and dTTP by klenow enzyme, leaving 5'-TC-3' at the 5' end. Genomic DNA isolated from the YAC clone of interest is partially digested with a suitable restriction enzyme, for example Sau3AI, and fractioned by sucrose-density gradient centrifugation to yield small DNA fragments (30–100 kb). Fragmented DNA is then partially filled in with dATP and dGTP by Klenow enzyme, leaving 5'-GA-3' at the 5' end. Ligation is performed using 0.5 µg of vector and from 1 to 2 µg, preferably 1.2 µg, of genomic DNA by a standard method and packaged with in vitro packaging extracts (Gigapack Gold, commercialized by Stratagene).

Then, cosmid clones are spread on LB agar plates containing 50 µg/ml of ampicillin at a density of 10 colonies/cm$^2$, and clones containing human DNA inserts are selected by colony hybridization with $^{32}$P-labelled human genomic DNA as a probe. Positive clones are picked up, incubated in 96-well microtiters plates, and stored at –70° C. A selection of these clones are purified by standard procedures. All the technical details regarding the preparation of a cosmid library is described by Yamakawa et al. (1991), the Materials and Methods section of this article being herein incorporated by reference.

In order to construct a contig map of the above selected cosmids, five ng of each cosmid DNA is digested with a restriction endonuclease, preferably EcoRI, electrophoresed on 1.0% agarose gels, and subjected to Southern blotting, using each cosmid as a probe. To suppress background signals generated by repetitive sequences present in cosmid inserts, an excess of total human DNA is prehybridized with each radiolabelled probe before hybridisation begins. The contig map of these cosmid clones is constructed on the basis of the hybridization patterns.

Then, exon amplification is performed as described by Buckler et al. (1991), the Materials and Methods section of this article being herein incorporated by reference. Briefly, fragments of cosmid DNAs are subcloned into a plasmid vector, pSPL1, and transfected into COS-7cells by electroporation. Reverse transcriptase (RT)-PCR products are isolated from cytoplasmic RNA of their transfectants and confirmed by Southern Hybridisation to have originated from the appropriate cosmid clones.

After exon amplification of the selected cosmid clones to search for transcribable sequences, the exon-like sequences are isolated, said exon-like sequences being subsequently used as probes to screen cDNA libraries, preferably cDNA libraries from fetal or adult liver (for example the adult liver cDNA libraries commercialized by Gibco/BRL or Clonetech).

Then, Northern blot analyses are performed using Multitissue blots obtained from Clontech labs (Palo Alto, Calif.). Prehybridization, hybridization are performed according to the manufacturer's recommendation in a solution containing 50% formamide, 5×Denhardt's solution, 6×SSC and 1% salmon sperm DNA. A restriction endonuclease (for example EcoRI/XhoI) cleavage product of the cDNA insert is used as a probe. Filters are then washed in 0.1×SSC/0.1% SDS at 50° C. for 20 min twice.

The cDNA clones thus selected are used to examine a panel of DNAs isolated from hepatocellular carcinomas for somatic rearrangements in the candidate sequences by means of Southern blot analyses with at least one of the selected cDNA clones as probe. Fluorescence in situ hybridization using such cDNA clones permits the detection of somatic rearrangement in DNA of HCC tumors. A comparison of the hybridization pattern of HCCs DNA with corresponding normal DNA will indicate that the rearrangement of the candidate cDNA has occurred as a somatic event.

The further step consists in sequencing the selected cDNA clone, which had been obtained from the fetal or adult liver cDNA library that will allow the structural analysis of the encoded candidate tumor suppressor gene and the comparison of its sequence with the other gene sequences that are compiled in the gene databases such as Genbank or EMBL databases.

The present invention is also directed to a method for isolating and /or purifying a tumor suppressor gene polynucleotide involved in the occurrence of a HCC in a patient comprising the steps of:

a) Constructing a cosmid library from a selected YAC clone;
b) Selecting cosmid clones of interest by colony hybridizattion with labelled human genomic DNA as a probe;
c) Constructing a contig map of the purified selected cosmid clones;
d) Performing an exon amplification reaction and inserting the reverse transcribed RNA fragments in a suitable vector;
e) Hybridizing the inserts of step d) to a suitable human cDNA library, preferably a fetal or adult liver cDNA library, and selecting the hybridizable cDNA clones;
f) Sequencing the selected cDNA clones inserts and characterizing the coding sequences;

The invention also concerns a tumor suppressor gene polynucleotide involved in the occurrence of a HCC in a patient obtained according to the above-described method.

Another subject of the present invention consists in a fragment of the tumor suppressor gene polynucleotide obtained by restriction enzyme cleavage or chemical synthesis.

The resulting polynucleotide sequences of the mutated variants and/or their above-described fragments are then used as specific oligonucleotide probes or primers for detecting mutations in (healthy or cancerous) patients, thus permitting the diagnosis of the predisposition of a given patient for HCC.

Advantageously, a nucleotide probe or primer as defined herein above has a length of at least 8 nucleotides, which is the minimal length that has been determined to allow a specific hybridization with the selected candidate tumor suppressor gene. Generally, said nucleotide probes have a nucleotide length ranging from 8 to 1000 nucleotides, preferably from 8 to 200 nucleotides and most preferably, the nucleic fragment has a length of at least 12 nucleotides, specifically 20 consecutive nucleotides of any of the selected candidate tumor suppressor gene.

These nucleic fragments may be used as primers for use in amplification reactions, or as nucleic probes.

Thus, the polynucleotides of the selected candidate tumor suppressor gene or the nucleic fragments obtained from such polynucleotides are used to select nucleotide primers notably for an amplification reaction such as the amplification reactions further described.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using as nucleic probes the polynucleotides the selected candidate tumor suppressor gene, fragments thereof, oligonucleotides that are complementary to these polynucleotides or fragment thereof or their amplification products themselves.

Amplified nucleotide fragments are employed as probes used in hybridization reactions in order to detect the presence of one polynucleotide according to the present invention or in order to detect mutations in the the selected candidate tumor suppressor gene.

Are also part of the present invention the amplified nucleic fragments (<<amplicons >>) defined herein above.

These probes and amplicons may be radioactively or non-radioactively labelled, using for example enzymes, such as those described in the U.S. Pat. No. 4,581,333 (Kourilsky et al.), or fluorescent compounds.

The primers may also be used as oligonucleotide probes to specifically detect a polynucleotide according to the invention.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recogntion site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.
b) The exponential amplification of these DNA molecules modified as such, by ezyme cleavage, strand displacement and copying of the displaced strands. The steps of cleavage, strand displacement and copy are repeated a sufficient number of times in order to obtain an accurate sensitivity of the assay.

The SDA technique was initially realized unsing the restriction endonuclease HincII but is now generally practised with an endonuclease from *Bacillus stearothermophilus* (BSOBI) and a fragment of a DNA polymerase which is devoid of any 5'→3'exonuclease activity isolated from *Bacillus cladotenax* (exo- Bca) [=exo-minus-Bca]. Both enzymes are able to operate at 60° C. and the system is now optimized in order to allow the use of dUTP and the decontamination by UDG. When unsing this technique, as described by Spargo et al. in 1996, the doubling time of the target DNA is of 26 seconds and the amplification rate is of $10^{10}$ after an incubation time of 15 min at 60° C.

The SDA amplification technique is more easy to perform than PCR (a single thermostated waterbath device is necessary) and is faster than the other amplification methods.

Thus, another object of the present invention consists in using the nucleic acid fragments according to the invention (primers) in a method of DNA or RNA amplification according to the SDA technique. For performing of SDA, two pairs of primers are used: apair of external primers (B 1, B2) consisting in a sequence specific of the target polynucleotide of interest and a pair of internal primers (S1, S2) consisting in a fusion oligonucleotide carrying a site that is recognized by a restriction endonuclease, for exemple the enzyme BSOBI.

As an illustrative embodiment of the use of the nucleotide probes and primers according to the invention in a SDA amplification reaction, a sequence that is non specific for the target polynucleotide and carrying a restriction site for HincII or BSOBI is added at the 5' end of a primer specific either for the selected candidate tumor suppressor gene. Such an additional sequence containing a restriction site that is recognized by BsoBI is advantageously the following sequence GCATCGAATGCATGTCTCGGGT, the nucleotides represented in bold characters corresponding to the recognition site of the enzyme BsoBI. Thus, primers useful for performing SDA amplification may be designed from any of the primers according to the invention as described above and are part of the present invention. The operating conditions to perform SDA with such primers are described in Spargo et al, 1996.

More specifically, the following conditions are used when preforming the SDA amplification reaction with the primers of the invention designed to contain a BsoBI restriction site: BsoBI/exo⁻Bca [=exo-minus-Bca] SDA reactions are performed in a 50 $\mu$l volume with final concentrations of 9.5 mM $MgCl_2$, 1.4 mM each dGTP, dATP, TTP, dCTP-alpha-S, 100 $\mu$g/ml acetylated bovine serum albumin, 10 ng/ml human placental DNA, 35 mM $K_2HPO_4$ pH 7.6, 0.5 $\mu$M primers S $1_{BsoBI}$ and B2 $_{BsoBI}$, 0.05 $\mu$M primers $B1_{BsoBI}$ and $B2_{BsoBI}$, 3.2 U/$\mu$l BsoBI enzyme, 0.16 U/$\mu$l exo⁻Bca [=exo-minus-Bca] enzyme, 3 mM Tris-HCl, 11 mM NaCl, 0.3 mM DTT, 4 mM KCl, 4% glycerol, 0.008 mM EDTA, and varying amounts of target DNA. Prior to the addition of BsoBI and exo⁻Bca, icomplete reactions (35 $\mu$l) are heated at 95° C. for 3 min to denature the target DNA, followed by 3 min at 60° C. to anneal the primers. Following the addition of a 15 $\mu$l enzyme mix consisting of 4 $\mu$l of BsoBI (40 Units/$\mu$l), 0.36 $\mu$l exo⁻Bca (22 Units/$\mu$l), and 10.6 $\mu$l enzyme dilution buffer (10 mM Tris Hcl, 10 mM $MgCl_2$, 50 mM NaCl, 1 mM DTT), the reactions are incubated at 60° C. for 15 min. Amplfication is terminated by heating for 5 min in a boiling water bath. A no-SDA sample is created by heating a sample in a boiling water bath immediately after enzyme addition. Aerosol resistant tips from Continental Laboratory Products are used to reduce contamination of SDA reactions with previously amplified products.

The polynucleotides of the selected candidate tumor suppressor gene and their above described fragments, especially the primers according to the invention, are useful as technical means for performing different target nucleic acid amplification methods such as:

TAS (Transcription-based Amplification System), described by Kwoh et al. in 1989;
SR (Self-Sustained Sequence Replication), described by Guatelli et al.in 1990.
NASBA (Nucleic acid Sequence Based Amplification), described by Kievitis et al. in 1991.
TMA (Transcription Mediated Amplification).

The polynucleotides of the selected candidate tumor suppressor gene and their above described fragments, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991 who employ a thermostable ligase.

RCR (Repair Chain Reaction) described by Segev et al. in 1992.

CPR ( Cycling Probe Reaction), described by Duck et al. in 1990.

Q-beta replicase reaction, described by Miele et al. in 1983 and improved by Chu et al. in 1986, Lizardi et al. in 1988 and by Burg et al. and Stone et al. in 1996.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

Nucleotide probes or polynucleotides according to the present invention are specific to detect the presence or the absence of a nucleotide sequence linked to the occurrence of HCC in the hummn genome. By <<specific probes>> according to the invention is meant any oligonucleotide that hybridizes with one polynucleotide the selected candidate tumor suppressor gene and which does not hybridize with unrelated sequences. Preferred oligonucleotide probes according to the invention are at least 8 nucleotides in length, and more preferably a length comprised between 8 and 300 nucleotides.

The oligonucleotide probes according to the present invention hybridize specifically with a DNA or RNA molecule comprising all or part of one polynucleotide among the selected candidate tumor suppressor gene under stringent conditions.

As an illustrative embodiment, the stringent hybridization conditions used in order to specifically detect a polynucleotide according to the present invention are advantageously the followings:

The hybridization step is realized at 65° C. in the presence of 6×SSC buffer, 5×Denhardt's solution, 0,5% SDS and 100 μg/ml of salmon sperm DNA.

The hybridization step is followed by four washing steps: two washings during 5 min, preferably at 65° C. in a 2×SSC and 0.1% SDS buffer;
one washing during 30 min, preferably at 65° C. in a 2×SSC and 0.1% SDS buffer,
one washing during 10 min, preferably at 65° C. in a 0.1×SSC and 0.1% SDS buffer.

The non-labelled polynucleotides or oligonucleotides of the invention may be directly used as probes. Nevertheless, the polynucleotides or oligonucleotides are generally labelled with a radioactive element ($^{32}P$, $^{35}S$, $^{3}H$, $^{125}I$) or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the french patent N° FR-7810975 or by Urdea et al. or Sanchez-Pescador et al., 1988.

In the latter case, other labeling techniques may be also used such those described in the french patents FR-2,422, 956 and 2,518,755. The hybridization step may be performed in different ways (Matthews et al., 1988). The more general method concists in immobilizing the nucleic acid that has been extracted from the biological sample on a substrate (nitrocellulose, nylon, polystyren) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European patent N° EP-0225,807 (Chiron).

In another advantageous embodiment of the probes according to the present invention, the latters may be used as <<capture probes>>, and are for this purpose immobilized on a substrate in order to capture the targer nucleic acid contained in a biological sample. The captured target nucleic acid is subsequently detected with a second probe which recognizes a sequence of the target nucleic acid which is different from the sequence recognized by the capture probe.

The oligonucleotide fragments useful as probes or primers according to the present invention may be prepared by cleavage of the polynucleotides of the selected candidate tumor suppressor gene by restriction enzymes, the one skill in the art being guided by the procedures described in Sambrook et al. in 1989.

Another appropriate preparation process of the nucleic acids of the invention containing at most 200 nucleotides (or 200 bp if these molecules are double stranded) comprises the following steps:

synthesising DNA using the automated method of beta-cyanethylphosphoramidite described in 1986;
cloning the thus obtained nucleic acids in an appropriate vector;
purifying the nucleic acid by hybridizing an appropriate probe according to the present invention.

A chemical method for producing the nucleic acids according to the invention which have a length of more thant 200 nucleotides nucleotides (or 200 bp if these molecules are double stranded) comprises the fllowing steps:

assembling the chemically synthsised oligonucleotides, having different restriction sites at each end.
cloning the thus obtained nucleic acids in an appropriate vector.
purifying the nucleic acid by hybridizing an appropriate probe according to the present invention.

In the case in which the above nucleic acids are used as coding sequences in order to produce a polypeptide according to the present invention, it is important to ensure that their sequences are compatible (in the appropriate reading frame) with the aminoacid sequence of the polypeptide to be produced.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary of a distinct sequence of the target nucleic acid. Optionally, the substrate of the matrix may be a material able to act as an electron donnor, the detection of the matrix poisitons in which an hybridization has occurred beeing subsequently determined by an electronic device. Such matrix libraries of probes and methods of specific detection of a targer nucleic acid is described in the European patent application N° EP-0713, 016 (Affymax technologies) and also in the U.S. Pat. No. 5,202,231 (Drmanac).

An oligonucleotide probe matrix may advantadgeously be used to detect mutations occurring in the selected candidate tumor suppressor gene. For this particular purpose, probes are specifically designed to have a nucleotidic sequence allowing their hybridization to the genes that carry known mutations (either by deletion, insertion of substitution of one or several nucleotides). By known mutations is meant mutations on the the selected candidate tumor suppressor gene that have been identified.

Another technique that is used to detect mutations in the the selected candidate tumor suppressor gene is the use of a high-density DNA array. Each oligonucleotide probe constituting a unit element of the high density DNA array is designed to match a specific subsequence of the the selected candidate tumor suppressor gene genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the the selected candidate tumor suppressor gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild refrence sequence. The hybridization signals of the 15-mer probe set tiled array are perturbed by a single base change in the target sequence. As a consequence, there is a caharacteristic loss of signal or a <<footprint>> for the probes flanking a mutation position. This technique was decribed by Chee et al. in 1996.

Another object of the present invention consists in hybrid molecule resulting from:
the hybrid formation between a DNA (genomic DNA or cDNA) or a RNA contained in a biological sample with a nucleic probe or primer according to the present invention;
the hybrid formation between a DNA (genomic DNA or cDNA) or a RNA contained in a biological sample with an amplified nucleic fragment obtained by the use of a pair of primers according to the present invention.

By cDNA according to the present invention is meant a DNA molecule that has been obtained by incubating an RNA molecule in the presence of an enzyme having a reverse transcriptase activity, as described by Sambrook et al. in 1989.

The present invention also pertains to a family of recombinant plasmids characterized in that they contain at least a nucleic acid according to the above teachings. According to an advantageous embodiment, a recombinant plasmid comprises a polynucleotide of the selected candidate tumor suppressor gene, or one nucleic fragment thereof.

Another object of the present invention consists in an appropriate vector for cloning, expressing or inserting a nucleic sequence, characterized in that it comprises a nucleic acid as above described in a site nonessential for its replication, optionally under the control of the regulation elements allowing the expression of a polypeptide of the invention.

Particular vectors used are plasmids, phages, cosmids, phagemids, PACs (P1 derived Artificial Chromosomes) and YACs (Yeast Artificial Chromosomes). As plasmids, pUC vectors are preferred.

Another object of the present invention consists in a method for detecting a genetic abnormality linked to the HCC in a biological sample containing DNA or cDNA, comprising the steps of:
a) bringing the biological sample into contact with a pair of oligonucleotide fragments according to the invention, the DNA contained in the sample having been optionally made available to hybridization and under conditions permitting a hybridization of the said oligonucleotide fragments with the DNA contained in the biological sample;
b) amplifying the DNA
c) revealing the amplification products;
d) optionally detecting a mutation or a deletion by appropriate techniques.

The step d) of the above-described method may consist in a Single-Starnd Polymorphism technique (SSCP), a Denaturing Gradient Gel Electrophoresis (DGGE), or the FAMA technique described in the PCT patent application N° WO-95/07361.

Another object of the present invention consists in a method for detecting a genetic abnormality linked to the HCC in a biological sample containing DNA or cDNA, comprising the steps of:
a) bringing the biological sample into contact with an oligonucleotide probe according to the invention, the DNA contained in the sample having been optionally made available to hybridization and under conditions permitting a hybridization of the primers with the DNA contained in the biological sample;
b) detecting the hybrid formed between the oligonucleotide probe and the DNA conatained in the biological sample.

The present invention consists also in a method for detecting a genetic abnormality linked to the HCC in a biological sample containing DNA, comprising the steps of:
a) bringing into contact a first oligonucleotide probe according to the invention that has been immobilized on a suuport, the DNA contained in the sample having been optionally made available to hybridization and under conditions permitting a hybridization of the primers with the DNA contained in the biological sample;
b) bringing into contact the hybrid formed between the immobilized first oligonucleotide probe and the DNA contained in the biological sample with a second oligonucleotide probe according to the invention, which second probe hybridizes with a sequence different from the sequence to which the immobilized first probe hybridizes, optionally after having removed the DNA contained in the biological sample which has not hybridized with the immobilized first oligonucleotide probe.

Another object of the present invention consists in a method for detecting a genetic abnormality linked to the HCC in a biological sample containing DNA, by the detection of the presence and of the position of base substitutions or base deletions in a nucleotide sequence included in a double stranded DNA preparation to be tested, the said method comprising the steps of:
a) amplifying specifically the region containing, on one hand, the nucleotide sequence of the DNA to be tested and on the other hand the nucleotide sequence of a DNA of known sequence, the DNA of known sequence being a polynucleotide according to the invention;
b) labeling the sense and antisense strands of these DNA with diferent fluorescent or other non-isotopic labels;
c) hybridizing the amplified DNAs;
d) revealing the heteroduplex formed between the DNA of known sequence and the DNA to be tested by cleavage of the mismatched parts of the DNA strands.

Such a mismatch localization technique has been described by Meo et al. in the PCT application N° WO-95/07361.

The invention also pertains to a kit for the detection of a genetic abnormality linked to the HCC in a biological sample, comprising the following elements:
a) a pair of oligonucleotides according to the invention;
b) the reagents necessary for carrying out a DNA amplification;
c) a component which makes it possible to determine the length of the amplified fragments or to detect a mutation.

The sequence of the identified candidate tumor suppressor gene allows the further screening for somatic mutations in HCC cancer cells, for example by single-strand polymorphism technique (SSCP).

SSCP analysis is performed by PCR amplification of each o the determined exons of the identified candidate tumor suppressor gene, correspoinding to the coding region, after having designed the suitable specific oligonucleotide primers, for example following the teachings of Rolfs et al.(1992). For this particular purpose, PCR reactions are carried out in 5 $\mu$l solutions containing 100 ng genomic DNA, 1 $\mu$M each primer, 25 $\mu$M dNTP, 2 $\mu$Ci of [$\alpha^{32}$P]dCTP (Amersham), and 0.25 U of Taq1 polymerase (Boehringer Mannheim). PCR products, which sow variant bands by SSCP analysis, are cloned into HindIII site of pBluescript SK(–) and the resulting independent clones are polled. Both strands are sequenced by the dideoxu chain-termination method with T7 DNA polymerase.

All the technical details regarding the cloning, identification and somatic mutation detection procedures of the candidate tumor suppressor gene are fully described by Fujiwara et al. (1991) and also by De Souza et al. (1995), the Materials and Methods section of these articles being herein incorporated by reference.

Other techniques for detecting the occurrence of a genetic alteration (insertions, deletions, substitutions) either generally in the chromosomal loci of interest identified by the inventors or in the specific sequences of the candidate suppressor genes determined as described herein before.

By performing a band shift assay, if the mutation in the selected candidate tumor suppressor gene is a deletion or insertion of one or more bases, a small segment of the gene—including the site of the mutation—is amplified by PCR, and the mutated allele detected by gel electrophoresis because of its altered mobility. Separation of 1 bp differences requires the incorporation of a radioactive label into the PCR product, followed by electrophoresis on a large denaturing polyacrylamide gel and autoradioragraphy. Differences of two or more bases are resolved on non-denaturing polyacrylamide gels, and the DNA fragments detected by staining with ethidium bromide (Sambrook et al., 1989).

Another technique of mutation analysis in the selected candidate tumor suppressor gene consists in a restriction site analysis (Halliassos et al., 1989, whose technical content is herein incorporated by reference) that is applied in the case in which the mutation occurs either by deleting or creating a restriction site in the sequence. In both cases, digestion of PCR product from the region of the mutation with the appropriate restriction enzyme will produce fragments of a different size if the mutation is present.

A third suitable procedure for detecting mutation in the selected candidate tumor suppressor gene consists in an allele-specific oligonucleotide assay, a technique in which the PCR product is spotted onto a nylon or notro cellulose membrane which is then incubated with a radioactively labelled oligonucleotide sequence of about 18 bases corresponding to either the normal or the mutant sequence (Conner et al., 1983; Saiki et al., 1986; Saiki et al., 1989).

The short oligonucleotide probes bind to their exact complementary sequence, provided that the tempreature and salt concentration of the solution used for the incubation are carefully controlled (see Rolfs et al., 1992 for the reagents concentrations determination). The oligonucleotide probe cans also be labelled with a non-radioactive tag such as biotin (Saiki et al., 1986)

The allele-specific priming technique is also very useful in order to detect genetic alterations in the selected candidate tumor suppressor gene. This technique utilizes the specificity of the PCR priming process to effect allele-specific priming of normal or mutant sequences (Newton et al., 1989; Ferrie et al., 1992). The allele-specific primer is so designed that its 3' end is located exactly at the site of mutation. PCR amplification occurs between this primer and a <<common primer>>, some distance away on the other side of the mutation, only if the sequence at the 3' end of the alle-specific primer matches the sequence of the sample DNA at this point.

In the case when the specific sequence of the mutation in the selected candidate tumor suppressor gene is unknown, various methods are used (reviewed by Dianzani et al., 1993; Grompe et al., 1993), the choice of a specific method among those available being governed by the size and the complexity of the gene to be screened and the degree of sensitivity required.

Single strand polymorphism has already been described above and the technical details regarding the procedures to follow in order to perform this technique are also found in the works described by Orita et al. (1989), Orita et al. (1989a), Yap et al. (1993), Hayashi et al. (1993).

The heteroduplex analysis method is based upon the observation that a hybrid between two single-stranded DNA molecules with sequences which differ from each other by single nucleotide has an altered conformation, which is detected as a reduction in electrophoretic mobility on non-denaturing gel. Briefly, the formation of heteroduplexes after PCR is encouraged by a bried denaturation step, followed by slow cooling at room temperature. The DNA is then electrophoresed in a non-denaturing gel of either polyacrylamide or Hydrolink (AT Biochem), and stained with ethidium bromide. The technical details regarding the specific procedures employed are described by Keen et al. (1991), White et al. (1992) and Soto et al. (1992).

The mutations occurring in the selected candidate tumor suppressor gene are also detected by the Denaturing gel electrophoresis (DGGE), a technique that exploits the fact that if a DNA fragment is electrophoresed at high temperature in a polyacrylamide gel which contains increasing concentrations of denaturants, it will become partially or completely denatured at some point. This event produces a sharp reduction in its electrophoretic mobility. Preferably, the sensitivity of the method is increased by the attachment of a GC-rich sequence (<<GC-clamp>>) to the end of the DNA fragment during PCR, which then serves as the last melting domain. Mutations of up to 600 bp are rapidly detected using the DGGE method. The specific procedures are descrobed by Grompe (1993), Fischer et al. (1983), Sheffield et al. (1989).

Are also used the Chemical cleavage method (CCM) and a very useful improvement of such a method which is FAMA. CCM is based upon the susceptibility of mismatched bases in a heteroduplex to modification by chemicals. DNA from the test sample and a radioactively labelled control is mixed, denatured, and allowed to form a heteroduplex. Incubation with hydroxylamine or osmium tetroxide results in modification of mismatched cytosines or thymines respectively, which are then cleaved with piperidine. The cleavage product produced by the mismatch is then detected by electrophoresis and autoradiography (Cotton et al., 1988; Montandon et al., 1989; Saleeba et al., 1992; Haris et al., 1994).

It is now easy to produce proteins in high amounts by the genetic engineering techniques by the use, as expression vectors, plasmids, phages or phagemids. The polynucleotides that code for the polypeptides of the present invention is inserted in an appropriate expression vector in order to in vitro produce the polypeptide of interest.

Thus, the present invention also concerns a method for the producing a polypeptide encoded by a candidate tumor suppressor gene of the invention, the said method comprising the steps of:
a) Optionally amplifying the nucleic acid coding for the desired polypeptide using a pair of primers according to the invention (by SDA, TAS, 3SR NASBA, TMA etc.).
b) Inserting the nucleic acid of interest in an appropriate vector;
c) culturing, in an appropriate culture medium, a cell host previously transformed or transfected with the recombinant vector of step b);
d) harvesting the culture medium thus conditioned or lyse the cell host, for example by sonication or by an osmotic shock;
e) separating or purifying, from the said culture medium, or from the pellet of the resultant host cell lysate the thus produced polypeptide of interest.
f) Characterizing the produced polypeptide of interest.

The polypeptides encoded to the candidate tumor suppressor genes according to the invention may be characterized by binding onto an immunoaffinity chromatography column on which polyclonal or monoclonal antiibodies directed to a polypeptide among the polypeptides of the selected candidate tumor suppressor gene have previously been immobilized, before their sequencing unsing the conventional protein sequencing methods well known from the one skill in the art.

The said antibodies may be prepared from hybridomas according to the technique described by Kohler and Milstein in 1975. The polyclonal antibodies may be prepared by immunisation of a mammal, especially a mouse or a rabbit, with a peptide according to the invention that is combined with an adjuvant of immunity, and then by purifying the specific antibodies contained in the serum of the immunized animal onto an affinity chromatography column on which has previously been immobilized the peptide that has been used as the antigen. A technique for preparing and using a immunoaffinity chromatography column is described, for example, by Bird et al. in 1984.

A preferred embodiment for preparing antibodies raised against the candidate tumor suppressor gene encoded protein is decribed hereafter. Briefly, the polypeptide of interest is conjugated to egg albumin (Calbiochem) using the benzidine-bis-diazoted procedure described by Gregory et al. in 1967, the ratio of polypeptide residues to one molecule of ovalbumin being 5:1. Rabbits are injected at time 0 with 1 mg of the conjugated polypeptide. Two months after the primary injection, animals are injected with 0.5 mg of the conjugated polypeptide and a thirs injection of 0.5 mg of the same polypeptide is performed between two and four months after the second injection. Antiserum is harvested between two and four weeks following the third conjugated polypeptide injection and optionally purified onto an affinity chromatography column as previously described. Preferably the injection is an intradermally multi-points injection; generally ten points of injection are performed.

The polypeptides according to the invention may also be prepared by the conventional methods of chemical synthesis, either in a homogenous solution or in solid phase. As an illustrative embodiment of such chemical polypeptide synthesis techniques, it may be cited the homogenous solution technique described by Houbenweyl in 1974.

The suitable promoter regions used in the expression vectors according to the present invention are choosen taking into account of the cell host in which the heterologous gene has to be expressed.

Preferred bacterial promoters are the LacI, LacZ, the T3 or T7 bacteriophage RNA polymerase promoters, the polyhedrin promoter, or the p10 protein promoter from baculovirus (Kit Novagen) (Smith et al., 1983; O'Reilly et al., 1992), the lambda $P_R$ promoter or also the trc promoter.

Preferred promoter for the expression of the heterologous gene in eukalyotic hosts are the early promoter of CMV, the Herpes simplex virus thymidine kinase promoter, the early or the late promoter from SV40, the LTR regions of certain retroviruses or also the mouse metallothionein I promoter.

The choice of a determined promoter, among the above-described promoters is well in the ability of one skill in the art, guided by his knowledge in the genetic engineering technical field, and by being also guided by the book of Sambrook et al. in 1989 or also by the procedures described by Fuller et al. in 1996.

Generally, suitable expression vectors used according to the present invention embrace plasmids, phages, cosmids or phagemids.

A suitable vector for the expression of the protein encoded by a candidate tumor suppressor gene above-defined or their peptide fragments is baculovirus vector that can be propagated in insect cells and in insect cell lines. A specific suitable host vector system is the pVL1392/1393 baculovirus transfer vector (Pharmingen) that is used to transfect the SF9 cell line (ATCC N° CRL 1711) which is derived from *Spodoptera frugiperda*.

Other suitable vectors for the expression of the protein encoded by a candidate tumor suppressor gene above-defined or their peptide fragments in a baculovirus expression system consist in plasmids which are baculovirus expression vectors with multiple cloning sites (MCS) that contain the specific expression elements of the pol gene in a pUC8 backbone. These plasmids can be divided into two subgroups, namely, on one hand the vectors pVLMelMyc-, which allow the construction of a N-terminal fucion to the signal sequence of the melittin gene (Chai et al., 1993; Vlasak et al., 1983) and on the other hand the vectors pVLPolMyc- which allow a N-terminal fusion to the first 12 aa of the pol and the c-Myc tag. The gene to be expressed can be cloned into the MCS, resulting in an N-terminal fusion to either the mel-myc or the pol-myc which are encoded by the vectors. An example of using such versatile vectors to express a mouse heterologous protein ($5HT_{5A}$ serotonin receptor) is notably described by Lenhardt et al. in 1996.

Another suitable vector for performing, the above-described process is a vaccinia virus vactor. In this specific embodiment, BSC-40 or LoVo are used for the transfection and culture steps.

Other particular expression vectors are the followings:
a) bacterial vectors : pBs, phagescript, PsiX174, pBluescript SK, pNH8a, pNH16a, pHN18a, pNH46a (all commercialized by Stratagene); pTrc99A, pKK223-3, pDR540, pRIT5 (all commercialized by Pharmacia); baculovirus transfer vector pVL1392/1393 (Pharmingen); pQE-30 (QIAexpress).

b) eukaryotic vectors: pWLneo, pSV2cat, pOG44, pXT1, pSG (all commercialized by Stratagene); pSVK3, pBPV, pMSG, pSVL (all commercialized by Pharmacia).

All the above-described vectors are useful to transform or transfect cell hosts in order to express a candidate tumor suppressor gene according to the present invention.

A cell host according to the present invention is characterized in that its genome or genetic background (including chromosome, plasmids) is modified by the heterologous polynucleotide gene sequence according to the present invention.

Preferred cell hosts used as recipients for the expression vectors of the invention are the followings:
a) Prokaryotic cells: *Escherichia coli* strains (I.E. DH5-α strain) or *Bacillus subtilis*.
b) Eukaryotic cell hosts: HeLa cells (ATCC N° CCL2; N° CCL2.1; N° CCL2.2), Cv 1 cells (ATCC N° CCL70), COS cells (ATCC N° CRL1650; N° CRL1651), Sf-9 cells (ATCC N° CRL1711).

The purification of the recombinant protein, peptide or oligomeric peptide according to the present invention may be realized by passage onto a Nickel or Cupper affinity chromatography column. The Nickel chromatography column may contain the Ni-NTA resin (Porath et al., 1975).

The peptides produced by genetic engineering methods according to the invention may be characterized by binding onto an immunoaffinity chromatography column on which polyclonal or monoclonal antibodies directed to the protein product of a candidate tumor suppressor gene according to the invention have previously been immobilized.

The present invention is further illustrated by the following Examples, without in anyway being limited in scope to the specific embodiments described in Examples.

EXAMPLES

I. Materials and Methods

A. Patients and DNA preparation. 120 primary HCCs and adjacent non-cancerous liver tissues were obtained from patients of various geographical origin who had undergone surgery. Frozen tissues were crushed and high molecular weight genomic DNAs were isolated as described previously (Nagai et al., 1994). Hepatitis B virus (HBV) integration was examined by Southern blotting using a $^{32}$P-labelled HBV DNA probe. The presence of HBsAg was analyzed using standard solid-phase radioimmunoassays (Abbott Laboratories). Serum anti-HCV Ab was measured by an enzyme-linked immunosorbent assay. TNM classification was applied to determine the tumor stage for each tumor (Hermanek and Sobin, 1987).

B. Microsatellite Repeat Amplification Analysis. A total of 120 HCCs were assayed for LOH by PCR with 195 selected primer pairs, designated as "panel A markers" from the collection of Généthon human genetic linkage map 1993–1994 (Gyapay et al., 1994). Each step of amplification, gel analysis and hybridization with (CA)n oligo probes were performed according to the large scale protocol as described in (Vignal et al., 1993). PCR was performed in a final 50 ml reaction volume including 50 ng of genomic DNA, 50 pmol of each primer, 1.25 mM dNTPs, 1 unit of Taq polymerase and 1xPCR buffer (10 mM Tris (pH9), 50 mM KCl, 1.5 mM $MgCl_2$, 0.1% Triton X-100 and 0.01% gelatin). Distribution of the various reagents was carried out using Hamilton AT plus robotics equipment (Hamilton, Switzerland). A "hot start" procedure was used in which the Taq polymerase was added only after an initial denaturation step of 5 min at 96° C. Amplification was carried out during 35 cycles of denaturation (94° C. for 40 sec) and annealing (55° C. for 30 sec). At the end of the last cycle, samples were incubated at 72° C. for 2 min for complete elongation. Six to eight of different marker products from the same individual were coprecipitated. Each coprecipitate was then dissolved in 5 ml of TE and mixed with 10 ml of deionized formamide and 2.5 ml of loading mix containing xylene cyanol blue and 50% sucrose. Samples were separated on 6% polyacrylamide gel in 8.3 M urea and then transferred onto nylon membrane by capillary blotting. Two to three different primers whose products did not overlap in size were selected, $^{32}$P end-labelled and used as hybridization probes. The membranes were serially hybridized at 42° C. several times using standard procedures.

C. Assessment of Loss of Heterozygosity. The signal intensity of each allele amplified from tumor DNA was compared with that from the corresponding normal counterpart DNA. Two reviewers (H.N., P.P.) evaluated the autoradiograms visually. Representative examples of autoradiograms showing AI are illustrated in FIG. 1. In a great majority of AI cases, we observed a marked reduction in the intensity of one allele in tumor DNA compared to normal DNA, consistent with allelic loss (FIG. 1A). The finding that a complete loss of one of the bands in tumor DNA track was rarely observed likely reflects the presence of normal, non parenchymal cells in tumor samples. A minor form of microsatellite abnormality in tumor DNA was allelic imbalance associated with increased signal intensity of one allele (FIG. 1A, T97) which may be interpreted as allelic gain (Kuroki et al., 1995; Yeh et al., 1994). Although the amount of the tumor and corresponding normal DNAs for PCR reaction was adjusted by repeated PCR experiments, we cannot firmly exclude that the dosage change of a given allele in HCC was due to gene amplification rather than allelic loss. We thus considered allelic imbalance, that includes both allelic loss and gain, as a representative value for loss of heterozygosity (LOH). Homozygotes were declared "not informative"(FIG. 1B).

D. Statistical Analysis. Relationships between clinicopathological characteristics and observed LOH were evaluated using $X^2$ test. The level of statistical significance was set at P<0.05.

Example 1

Allelotyping of HCC

We examined DNAs isolated from 120 paired HCC and adjacent non tumorous liver tissues for allelic imbalances. Serological studies revealed that among the 116 patients tested for hepatitis B virus (HBV) markers, 83 were positive for hepatitis B surface antigen (HBsAg) and among the 42 patients analyzed for hepatitis C virus (HCV) markers, 19 were HCV Ab positive, including 4 that were also positive for HBsAg. HBV DNA integration was observed in 33 HCC samples (31 among the HBsAg positive patients and 2 among the HBsAg negative).

Allelic imbalances were assayed by PCR with primer pairs that flank highly polymorphic CA microsatellites. We selected a panel of 195 representative markers (Table 1) mapping to 39 non-acrocentric autosomal arms and spanning a total distance of 3432 cM with 171 intervals, which corresponds to an average marker distance of 20 cM (range, 15–22 cM). The mean homozygosity of the microsatellite markers was 27%, a value which is comparable to that in the literature (Gyapay et al., 1994). In average, 73 tumors out of the 120 analyzed were informative.

A difference in the relative allele intensity ratios between tumor DNA and normal DNA in an informative tumor/normal pair was scored as loss of heterozygosity (see Materials and Methods). LOH affecting multiple chromosomal loci were observed in most tumors analyzed, with an average number of loci exhibiting LOH of 12.8 per tumor (range, 0–39). Only one tumor did not show any genetic alteration with the 195 markers tested suggesting that, in this case, a significant amount of non neoplastic DNA obscured the ability to detect allelic changes in the tumor DNA. Range of percentage LOH in informative tumors was from 0 to 42% with an average of 12.1±8.4% (mean±SD). Significant percentage of LOH was arbitrarily chosen to be a value above the mean (background) percentage LOH plus SD (20%). Three markers, D2S294, D10S249 and D2S171, did not show any LOH in 70, 79 and 95 informative HCC cases respectively.

A total of 33 markers corresponding to 26 distinct chromosomal regions revealed LOH in 20% or more of the tumors. A summary of the results is provided in Table 2. Among them, the highest rates of LOH were observed for specific loci on chromosome arms 2q36-q37 (29%), 4q35 (40%), 6q27 (36%), 7p15 (30%), 8p23 (42%), 13q12-q13 (30–32%), 16q23-q24 (28%) and 17p13(33%). The LOH detected at locus D8S277 in 8p23 with a frequency of 42% of 97 informative HCCs corresponds to the most frequent genetic alteration in our study. A number of chromosomal subregions found to be affected in our analysis had been already reported on chromosome arms 1p, 4q, 6q, 8p, 10q, 13q, 16p, 16q, 17p (Buetow et al., 1989; De Souza et al., 1995; Emi et al., 1992; Fujimori et al., 1991; Tsuda et al., 1990; Wang and Rogler, 1988; Yeh et al., 1994). In addition, we detected LOH in loci that had never been involved in previous studies, notably in 1q22-q23, 1q42-q43, 2q36-q37, 7p15-p22, 7q33-q34, 8q23-q24, 9p12-p14, 9q34-qter, 14q32 and 17q24-qter. We were able to define two noncontinuous significant regions of LOH on 1p (at 1p21-p22 and p36) and three on 4q (at 4q12-q21, q22-q24 and q35) indicating that several genes on chromosomes 1 and 4 may be targets of genetic alterations. On 8p and 13q, frequent LOH was found spanning a large region of three contiguous markers (D8S277, D8S550 and D8S282 for 8p, D13S171, D13S284 and D13S170 for 13q) suggesting the presence of more than one tumor suppressor gene in these regions.

Example 2
Genetic Alterations on Individual Chromosomal Arms and Clinicopathological Data As markers were distributed with equal intervals on each chromosome, the frequency of LOH per chromosome arms was analyzed (Table 3). Average percent LOH per chromosomal arm was 24.9±12.7%. In total, 119 out of the 120 HCC cases analyzed were informative for at least one locus on each of the 39 chromosome arms. Allelic changes occurring at a frequency of 25% (average) or more of informative HCC cases were on 1p (51%), 1q (44%), 2q (35%), 4q (52%), 6q (48%), 7p (28%), 7q (28%), 8p (40%), 8q (26%), 9p (33%), 9q (43%), 10q (25%), 13q (53%), 14q (34%), 16p (36%), 16q (31%), 17p (34%) and 17q (31%). Among the chromosome arms showing the highest frequencies of microsatellite abnormalities (☐31%), eight (1p, 4q, 6q, 8p, 13q, 16p, 16q and 17p) had been implicated in previous studies (Buetow et al., 1989; Emi et al., 1992; Fujimori et al., 1991; Tsuda et al., 1990; Wang and Rogler, 1988; Yeh et al., 1994) and six (1q, 2q, 9p, 9q, 14q and 17q) appear as new candidates for the search of tumor suppressor genes.

We were then interested in exploring a possible correlation between clinicopathological characteristics of the tumors and LOH. Because the limited number of samples showing LOH at each individual locus and for which clinicopathological parameters were available could not confer any significant statistical value, we performed the analysis at the level of each chromosomal arm. The data are summarized in Table 3. None of the chromosome arm alteration was statistically correlated with positive serum markers (HBsAg or HCVAb) for hepatitis virus infections. Although the relationship between LOH and the tumor stage could not be statistically evaluated because of the low number of early tumors, a tendency towards frequent LOH on 1p and 1q was observed in small HCCs classified as T1 (respectively 4 and 5 of 10 tumors). On the contrary, at this tumor stage, few changes were noted on 2q, 6q, 7q, 8q, 14q, 16pq and 17pq (0–1 of 10 tumors). Allelic imbalance on 16p and 17p appeared relatively frequently in invasive tumors having intrahepatic metastasis or portal vein invasions compared to non-invasive tumors (3-4/12 vs. 1/13 tumors). Pathological informations of the adjacent non-tumorous liver counterparts were obtained from 66 cases, 35 of which displayed chronic hepatitis (CH) lesions and the remainder (31) liver cirrhosis (LC). No statistically significative correlation was observed between the presence of genetic alterations on a particular chromosomal arm and the pathological state of the non tumorous liver. However, the frequency of LOH observed concomitantly on both arms 1p and 13q, 1p and 8p as well as 6q and 13q were significantly higher in tumors arising from CH than LC (the number of HCCs with CH vs. LC showing LOH in above combinations were 16 vs. 5, 16 vs. 6, and 14 vs. 3 respectively).

Conclusion

Genetic alterations frequently detected in human cancers include regional amplification of chromosome arms. In liver cancer, multiplication of a large region at 8q24 (Fujiwara et al., 1993) and of the distal part of chromosome 1p (Kuroki et al., 1995; Yeh et al., 1994) have been previously reported. Our recent comparative genomic hybridization analysis of HCC has revealed frequent increase in the copy number of chromosomal regions at 8q22-24, 1q 11-25, and, to a lesser extent, at chromosomes 6p and 17q (Marchio et al., 1997). These data suggest that a fraction of allelic imbalances in the loci described in the present study includes regional amplifications.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 1

195 PCR marker loci used for allelotyping.

| Chr. | Locus amplified |
|---|---|
| 1p | D1S243, D1S214, D1S228, D1S199, D1S255, D1S476, D1S198 D1S207, D1S248 |
| 1q | D1S305, D1S196, D1S238, D1S249, b1S229, D1S235, D1S304 |
| 2p | D2S281, D2S149, D2S171, D2S177, D2S378, D2S286 |
| 2q | D2S113, D2S347, D2S151, D2S294, D2S311, D2S143, D2S159, D2S125 |
| 3p | D3S1307, D3S1560, D3S1263, 3S1266, D3S1578, D3S1285 |
| 3q | D3S1276, D3S1572, D3S1292, D3S1279, D3S1282, D3S1262, D3S1265 |
| 4p | D4S412, D4S403, D4S391 |
| 4q | D4S392, D4S1538, D4S1578, D4S406, D4S430, D4S4221 D4S1548, D4S1597, D4S408, D4S426 |
| 5p | D5S416, D5S426, D5S392 |
| 5q | D5S407, D5S424, D5S495, D5S421, D5S393, D5S410, D5S400, D5S408 |
| 6p | D6S344, D6S309, D6S260, D6S276, D6S426, D6S294 |
| 6q | D6S462, D6S261, D6S292, D6S290, D6S305, D6S446, D6S281 |
| 7p | D7S531, D7S664, D7S493, D7S484, D7S519 |

TABLE 1-continued

195 PCR marker loci used for allelotyping.

| Chr. | Locus amplified |
|---|---|
| 7q | D7S669, D7S657, D7S486, D7S495, D7S483, D7S550 |
| 8p | D8S277, D8S550, D8S282, D8S283, D8S260 |
| 8q | D8S273, D8S281, D8S272 |
| 9p | D9S288, D9S156, D9S161, D9S273 |
| 9q | D9S153, D9S277, D9S195, D9S164, D9S158 |
| 10p | D10S249, D10S189, D10S191, D10S193 |
| 10q | D10S589, D10S185, D10S597, D10S587, D10S212 |
| 11p | D11S922, D11S1349, D11S904, D11S903 |
| 11q | D11S916, D11S934, D11S968 |
| 12p | D12S352, D12S77, D12S310, D12S87 |
| 12q | D12S82, D12S78, D12S86, D12S367, D12S83 |
| 13q | D13S175, D13S171, D13S284, D13S170, D13S158, D13S285, D13S286 |
| 14q | D14S261, D14S75, D14S63, D14S74, D14S81, D14S292 |
| 15q | D15S128, D15S165, D15S118, D15S153, D15S205, D15S120 |
| 16p | D16S521, D16S407, D16S420, D16S411 |
| 16q | D16S408, D16S518, D16S422, D16S520 |
| 17p | D17S926, D17S786, D17S953 |
| 17q | D17S933, D17S787, D17S949, D17S784, D17S928 |
| 18p | D18S59, D18S62, D18S453 |
| 18q | D18S57, D18S64, D18S61, D18S70 |
| 19p | D19S209, D19S4l3, D19S407 |
| 19q | D19S223, D19S219, D19S418, D19S210 |
| 20p | D20S175, D20S104 |
| 20q | D20S107, D20S109, D20S171, D20S207 |
| 21q | D21S1256, D21S263, D21S268 |
| 22q | D22S420, D22S315, D22S277, D22S274 |

Chr., chromosomal arms containing markers.

eb

TABLE 2

Summaries of microsatellite marker loci demonstrating significant percentage LOH in HCC allelotyping.

| Chromosomal location | Locus | LOH/informative cases | (%) |
|---|---|---|---|
| 1p36 | D1S199 | 25/97 | (26) |
|  | D1S255 | 23/93 | (25) |
| 1p21–p22 | D1S248 | 14/60 | (20) |
| 1q22–q23 | D1S238 | 14/70 | (20) |
| 1q42–q43 | D1S235 | 21/89 | (24) |
| 2q36–q37 | D2S336 | 23/79 | (29) |
|  | D2S125 | 19/92 | (20) |
| 4q12–q21 | D4S1538 | 24/115 | (21) |
| 4q22–q24 | D4S406 | 19/71 | (27) |
| 4q35 | D4S426 | 32/82 | (40) |
| 6q25 | D6S290 | 17/70 | (24) |
| 6q27 | D6S305 | 9/25 | (36) |
| 7p21–p22 | D7S664 | 18/69 | (26) |
| 7p15 | D7S493 | 21/80 | (30) |
| 7q33–q34 | D7S495 | 16/78 | (20) |
| 8p23 | D8S277 | 41/97 | (42) |
|  | D8S550 | 17/79 | (21) |
|  | D8S282 | 14/62 | (22) |
| 8q23–q24 | D8S263 | 14/61 | (23) |
| 9p12–p14 | D9S273 | 17/79 | (21) |
| 9q34–qter | D9S164 | 16/81 | (20) |
| 10q26 | D10S587 | 15/63 | (24) |
|  | D10S212 | 14/52 | (27) |
| 13q12–q13 | D13S171 | 24/74 | (32) |
| 13q14 | D13S284 | 25/83 | (30) |
|  | D13S170 | 24/104 | (23) |
| 13q21–q32 | D13S158 | 21/104 | (20) |
| 14q32 | D14S81 | 17/82 | (23) |
| 16p11–p13 | D16S420 | 16/74 | (22) |
| 16q23–q24 | D16S422 | 21/75 | (28) |
| 17p13 | D17S786 | 25/76 | (33) |
|  | D17S953 | 9/40 | (22) |
| 17q24–qter | D17S928 | 13/61 | (21) |

TABLE 3

Significant allelic loss for chromosomal arms and correlation with clinicopathologic characteristics in 120 HCCs.

| Chromosomal arm | LOH (n) | | | | | | | | | | | | | | | | | |
|---|---|---|---|---|---|---|---|---|---|---|---|---|---|---|---|---|---|---|
|  | 1p | 1q | 2q | 4q | 6q | 7p | 7q | 8p | 8q | 9p | 9q | 10q | 13q | 14q | 16p | 16q | 17p | 17q |
| LOH (%) | 51 | 44 | 35 | 52 | 48 | 28 | 28 | 40 | 26 | 33 | 43 | 25 | 53 | 34 | 36 | 31 | 34 | 31 |
| Hepatitis virus markers | | | | | | | | | | | | | | | | | | |
| HBsAg+ (n = 83) | 46 | 35 | 32 | 47 | 49 | 23 | 29 | 35 | 22 | 28 | 42 | 23 | 49 | 31 | 36 | 20 | 28 | 14 |
| HBsAg– (n = 33) | 13 | 16 | 8 | 14 | 5 | 8 | 4 | 11 | 5 | 9 | 7 | 6 | 13 | 8 | 6 | 5 | 9 | 15 |
| HBVint+ (n = 33) | 17 | 12 | 11 | 16 | 17 | 15 | 12 | 14 | 7 | 10 | 14 | 9 | 19 | 10 | 12 | 11 | 8 | 6 |
| HBVint– (n = 45) | 25 | 18 | 17 | 17 | 15 | 13 | 11 | 18 | 10 | 13 | 13 | 13 | 22 | 14 | 10 | 7 | 15 | 11 |
| HCV Ab+ (n = 19) | 7 | 8 | 5 | 6 | 3 | 6 | 4 | 6 | 1 | 4 | 2 | 6 | 7 | 3 | 3 | 3 | 2 | 5 |
| HCV Ab– (n = 23) | 16 | 8 | 6 | 12 | 9 | 4 | 8 | 12 | 7 | 7 | 6 | 9 | 17 | 9 | 7 | 6 | 10 | 3 |
| Clinicopathological findings | | | | | | | | | | | | | | | | | | |
| T1 (n = 10) | 4 | 5 | 1 | 2 | 1 | 2 | 1 | 3 | 1 | 2 | 3 | 2 | 3 | 1 | 1 | 0 | 1 | 1 |
| T2–4 (n = 46) | 27 | 19 | 17 | 25 | 15 | 14 | 11 | 19 | 10 | 12 | 14 | 17 | 25 | 16 | 13 | 11 | 13 | 15 |
| IHM/PVI+ (n = 12) | 6 | 3 | 2 | 3 | 2 | 2 | 1 | 6 | 2 | 2 | 2 | 4 | 6 | 2 | 4 | 1 | 3 | 4 |
| IHM/PVI– (n = 13) | 7 | 8 | 3 | 7 | 2 | 2 | 2 | 7 | 2 | 4 | 5 | 2 | 6 | 4 | 1 | 1 | 1 | 4 |

TABLE 3-continued

Significant allelic loss for chromosomal arms and correlation with clinicopathologic characteristics in 120 HCCs.

| Chromosomal arm | LOH (n) | | | | | | | | | | | | | | | | |
|---|---|---|---|---|---|---|---|---|---|---|---|---|---|---|---|---|---|
| | 1p | 1q | 2q | 4q | 6q | 7p | 7q | 8p | 8q | 9p | 9q | 10q | 13q | 14q | 16p | 16q | 17p | 17q |
| Non tumorous liver | | | | | | | | | | | | | | | | | | |
| CH (n = 35) | 24 | 13 | 14 | 16 | 15 | 13 | 15 | 19 | 8 | 12 | 10 | 9 | 23 | 12 | 10 | 10 | 11 | 5 |
| LC (n = 31) | 14 | 14 | 9 | 17 | 6 | 9 | 3 | 9 | 7 | 9 | 8 | 11 | 13 | 7 | 8 | 5 | 6 | 15 |

T1–4, TNM classification of HCC; IHM/PVI, intrahepatic metastasis and portal vein invasion; CH, chronic hepatitis; LC, liver cirrhosis; +, positive; −, negative.

TABLE 4

Summaries of microsatellite marker loci demonstrating significant percentage LOH in HCC allelotyping. Refinement of the mapping presented in Table 2.

| Microsatellite markers | Number of LOH occurrences | Number of informative cases | Percentage of LOH |
|---|---|---|---|
| 8p23 | | | |
| D8S264 | | 67 | 35 |
| D8S262 | | 50 | 39 |
| D8S1140 | ND | ND | ND |
| D8S518 | | 57 | 47 |
| D8S1099 | | | 46 |
| D8S1742 | | 54 | 53 |
| D8S277 | | 55 | 43 |
| D8S561 | | | 38 |
| D8S1819 | | 50 | 43 |
| 8p22 | | | |
| D8S1469 | | 40 | 50 |
| D8S1721 | | 47 | 42 |
| D8S550 | | | 22 |
| D8S552 | | 55 | 18 |
| D8S1731 | | 52 | 38 |
| D8S261 | | | 41 |
| 8p21 | | | |
| D8S282 | | | 21 |
| D8S1752 | | 62 | 39 |
| D8S1771 | | | 33 |
| D8S1820 | | | 30 |
| D8S213 | | | 2 |
| D8S532 | | | 16 |
| D8S285 | | | 9 |
| D8S260 | | | 15 |
| 1p35–p36 | | | |
| D1S228 | 3 | 39 | 8 |
| D1S436 | 8 | 25 | 32 |
| D1S2644 | 15 | 30 | 50 |
| D1S199 | 25 | 50 | 50 |
| D1S2843 | 8 | 30 | 27 |
| D1S478 | 18 | 28 | 64 |
| D1S2828 | 6 | 9 | 67 |
| D1S2902 | 5 | 18 | 28 |
| D1S247 | 17 | 31 | 55 |
| D1S255 | 24 | 50 | 48 |
| 16q23–q24 | | | |
| D16S507 | 10 | 28 | 36 |
| D16S3098 | 10 | 15 | 67 |
| D16S505 | 13 | 15 | 87 |
| D16S511 | 12 | 14 | 86 |
| D16S422 | 21 | 25 | 84 |
| D16S402 | 12 | 19 | 63 |
| 14q32 | | | |
| D14S74 | 2 | 12 | 17 |
| D14S280 | 5 | 10 | 50 |
| D14S995 | 5 | 14 | 36 |
| D14S977 | 2 | 10 | 20 |
| D14S81 | 16 | 28 | 57 |
| D14S1062 | 5 | 24 | 21 |
| D14S265 | 7 | 12 | 58 |
| D14S292 | 6 | 17 | 35 |
| 4q35–q36 | | | |
| D4S392 | 14 | 38 | 37 |
| D4S3042 | 7 | 12 | 58 |
| D4S2922 | 7 | 12 | 58 |
| D4S400 | 7 | 9 | 78 |
| D4S395 | 7 | 20 | 35 |
| D4S1534 | 6 | 16 | 38 |
| D4S2929 | 4 | 15 | 27 |
| D4S2460 | 8 | 15 | 53 |
| D4S1578 | 9 | 45 | 20 |
| D4S1572 | 9 | 14 | 64 |
| D4S1564 | 11 | 16 | 69 |
| D4S2945 | 9 | 14 | 64 |
| D4S1616 | 6 | 10 | 60 |
| D4S2937 | 11 | 17 | 65 |
| D4S1613 | 8 | 11 | 45 |
| D4S427 | 5 | 11 | 45 |
| D4S430 | 14 | 42 | 33 |

ND = Not Determined
Blank cell: Non Represented or Not Done

References

Barany F., 1911, Proc. Natl. Acad. Sci. USA, 88:189–193.
Becker S. A. et al., 1996, Cancer Res., 56:5092–5097.
Boige V. et al., 1996, Proc. of the Am. Assoc. for Cancer Res., 37:551.
Bosch F. X. et al., 1991, Adv. Appl. Biotechnol., 13:35–56.
Bressac B. et al., Proc. Natl. Acad. Sci. USA, 87:1973–1977.
Bressac, B., Kew, M., Wands, J. and Ozturk, M. (1991). *Nature* (*London*), 350, 429–431.
Buendia, M. A. and Pineau, P. (1995). *DNA tumor viruses: oncogenic mechanisms*. Barbanti-Brodano, G., Bendinelli, M. and Friedman, H. (eds). Plenum Press: New York, pp 171–193.
Bird P., 1984, J. Immunol. Methods, 71:97–105.

Buetow, K. H., Murray, J., Israel, J., London, W., Smith, M., Kew, M., Blanquet, V., Bréchot, C., Redeker, A. and Govindarajah, S. (1989). *Proc. Natl. Acad. Sci. USA*, 86, 8852–8856.

Buetow, K. H., Sheffield, V. C., Zhu, M., Zhou, T., Shen, F. M., Hino, O., Smith, M., McMahon, B. J., Lanier, A. P., London, W. T., Redeker, A. G. and Govindarajan, S. (1992). *Proc. Natl. Acad. Sci. USA*, 89, 9622–9626.

Burg J. L. et al., 1996, Mol. and Cell. Probes, 10:257–271.

Call, K. M., Glaser, T., Ito, C. Y., Buckler, A. J., Pelletier, J. et al. (1990). *Cell*, 60, 509–520.

Chai H. et al., 1993, Biotechnol. Appl. Biochem., 18:259–273.

Chee et al., 1996, Science, 274:610–614

Chen C. et al., 1986, Br. J. Exp. Pathol., 67:1868.

Chu B. C. F. et al., 1986, Nucleic Acids Res., 14:5591–5603.

Conner B. J. et al., 1983, Proc. Natl. Acad. Sci., 80:278–282.

Cotton R. G. et al., Proc. Natl. Acad. Sci., 85:4397–4401.

Cox, D. W., Gedde-Dahl, T., Menon, A. G., Nygaard, T. G., Tomlinson, I. M., Peters, J., St. George-Hyslop, P. H., Walter, M. A. and Edwards, J. H. (1995). *Cytogenet. Cell Genet.*, 69, 160–178.

De Souza, A. T., Hankins, G. R., Washington, M. K., Orton, T. C. and Jirtle, R. L. (1995). *Nat. Genet.*, 11, 447–449.

De Thé H. et al., 1987, Nature, 330:667–670.

Dejean, A., Bougueleret, L., Grzeschik, K. H. and Tiollais, P. (1986). *Nature (London)*, 322, 70–72.

Dianzani I. et al., 1993, Trends Genet., 9(12):403–405.

Dib C., Fauré S., Fizames C., Samson D., Drouot N., Vignal A., Millasseau P., Marc S., Hazan J., Seboun E., Lathrup M., Guyapay G., Morissette J. and Weissenbach J. <<A comprehensive genetic map of the human genome based on 5264 microsatellites >>, 1996, Nature, 380:152–154.

Duck P. et al., 1990, Biotechniques, 9:142–147.

Emi, M., Fujiwara, Y., Nakajima, T., Tsuchiya, E., Tsuda, H., Hirohashi, S., Maeda, Y., Tsuruta, K., Miyaki, M. and Nakamura, Y. (1992). *Cancer Res*, 52, 5368–5372.

Fearon, E. R., Cho, K. R., Nigro, J. M., Kern, S. E., Simons, J. W. et al (1990). *Science*, 247, 49–56.

Ferrie M. et al., 1992, Am. J. Human Genet., 51:251–262.

Fischer S. G. et al., 1983, Proc. Natl. Acad. Sci. USA, 80:1579–1583.

Friend, S. H., Bernards, R., Rogelij, S., Weinberg, R. A., Rapaport, J. M., Albert, D. M. and Dryja, T. P. (1986). *Nature (London)*, 323, 643–646.

Fujimori, M., Tokino, T., Hino, O., Kitagawa, T., Imamura, T., Okamotto, E.,

Mitsunobu, N., Ishikawa, T., Nakagama, H., Harada, H., Yagura, M.,

Matsubara, K. and Nakamura, Y. (1991). *Cancer Res*, 51, 89–93.

Fujiwara, Y., Monden, M., Mori, T., Nakamura, Y. and Emi, M. (1993). *Cancer Research*, 53, 857–860.

Fujiwara, Y., Ohata, H., Kuroki, T., Koyama, K., Tsuchiya, E., Monden, M. and Nakamura, Y. (1995). *Oncogene*, 10, 891–895.

Fuller S. A. et al., 1996, Immunology in Current Protocols in Molecular Biology, Ausubel et al. Eds, John Wiley & Sons, Inc., USA.

Gregory D. W., 1967, Bochim. Biophys. Acta, 133:319–332.

Grompe et al., 1993, Nature Genet., 5:111–117.

Guateli J. C. et al., 1990, Proc. Natl. Acad. Sci. USA, 87:1874–1878.

Gyapay, G., Morissette, J., Vignal, A., Dib, C., Fizames, C., Millasseau, P., Marc, S., Bernardi, G., Lathrop, M. and Weissenbach, J. (1994). *Nature Gen*, 7, 246–249.

Hahn, S. A., Schutte, M., Hoque, A. T. M. S., Moskaluk, C. A., da Costa, L. T., Rozenblum, E., Weinstein, C. M., Fischer, A., Yeo, C. J., Hruban, R. H. and Kern, S. E. (1996). *Science*, 271, 350–353.

Halliassos et al., 1989, Nucleic Acids Res., 17:3606

Hansen M. F. et al., 1987, Cancer Res., 47:5518.

Haris I. I. et al., 1994, PCR Methods and Applications, 3:268–271.

Hayashi K. et al., Hum. Mutat., 2:338–346.

Hearly, E., Rehman, I., Angus, B. and Ress, J. R. (1995). *Genes Chromosomes Cancer*, 12, 152–156.

Hermanek, P. and Sobin, L. H. (eds) (1987). *TNM classification of malignant tumors*, 4th Ed edn. Springer, Berlin.

Houbenweyl, 1974, in Meuthode der Organischen Chemie, E. Wunsch Ed., Volume 15-I et 15-II, Thieme, Stuttgart.

Hsu, I. C., Metcalf, R. A., Sun, T., Welsh, J. A., Wang, N. J. and Harris, C. C. (1991). *Nature (London)*, 350, 427–428.

Isola J. et al., 1994, Am. J. Pathol., 145(6):1301–1308.

Kallioniemi O. P. et al., 1994, Genes Chromosomes Cancer, 10:231–243.

Keen J. et al., 1991, Trends Genet., 7:5.

Kievitis T. et al., 1991, J. Virol. Methods, 35:273–286.

Kohler G. et al., 1975, Nature, 256(5517):495–497.

Kuroki, T., Fujiwara, Y., Tsuchiya, E., Nakamori, S., Imaoka, S., Kanematsu, T. and Nakamura, Y. (1995). *Genes Chromosomes Cancer*, 13, 163–167.

Kwoh D. Y. et al., 1989, Proc. Natl. Acad. Sci. USA, 86:1173–1177.

Landegren U. et al., 1988, Science, 241:1077–1080.

Lenhard T. et al., 1996, Gene, 169:187–190.

Lizardi P. M. et al., 1988, Bio/technology, 6:1197–1202.

Lok A. S. F. et al., 1991, Hepatology, 13:834–837.

Marchio, A., Meddeb, M., Pineau, P., Danglot, G., Tiollais, P., Bernheim, A. and Dejean, A. (1997). *Genes Chromosomes Cancer*, 18:59–65.

Matsubara, K. (1991). *Molecular Biology of the Hepatitis B Virus*. McLachlan, A. (ed.). CRC Press, Inc.: Boca Raton, Fla., pp 245–256.

Matthews J. A. et al., 1988, Anal. Biochem., 169:1–25.

Miki, Y., Swensen, J., Shattuck-Eidens, D., Futreal, P. A., Harshman, K. et al (1994). *Science*, 266, 66–71.

Montandon A. J. et al., 1989, Nucleic Acids Res., 17:3347–3358.

Murakami, Y., Hayashi, K., Hirohashi, S. and Sekiya, T. (1991). *Cancer Res.*, 51, 5520–5525.

Nagai, H., Ponglikitmongkol, M., Mita, E., Ohmachi, Y., Yoshikawa, H., Saeki, R., Yomuto, Y., Nakanishi, T. and Matsubara, K. (1994). *Cancer Res*, 54, 1545–1550.

Newton C. R. et al., 1989, Nucleic Acids Res., 17:2503–2517.

O'Reilly et al., 1992, Baculovirus expression vectors: a Laboratory Manual. W. H. Freeman and Co., New York.

Okuda K. et al., 1992, Hepatology, 15:948–963.

Orita M. et al., 1989, Proc. Natl. Acad. Sci. USA, 86:2766–2770.

Orita M. et al., 1989a, Genomics, 5:874–879.

Ranford, D. M., Fair, K. L., Philips, N. J., Ritter, J. H., Steinbruek, T., Holt, M. S. and Donnis-Keller, H. (1995). *Cancer Res.*, 55, 3399–3405.

Rolfs A. et al., 1992, In: PCR: Clinical diagnostics and research, Springer-Verlag, Berlin, 1–20.

Saiki R. K. et al., 1986, Nature, 324:163–166.

Saiki R. K. et al., 1989, Proc. Natl. Acad. Sci. USA, 86:6230–6234.

Saleeba J. A. et al., 1992, Hum. Mutat., 1:63–69.

Sambrook, J. et al. 1989. In Molecular cloning: A Laboratory Manual. Cold Spring Harbor, N.Y.: Cold Spring Harbor Laboratory Press.

Sheffield V. C. et al., 1989, Proc. Nat. Acad. Sci. USA, 86:232–236.

Shimizu M. et al., 1990, Oncogene, 5:185–194.
Slagle B. L. et al., 1991, Cancer Res., 51:49–54.
Slagle, B. L., Zhou, Y. Z. and Butel, J. S. (1991). *Cancer Res.,* 51, 49–54.
Slagle, B. L., Zhou, Y. Z., Birchmeier, W. and Scorsone, K. A. (1993). *Hepatology,* 18, 757–762.
Smith et al., 1983, Mol. Cell. Biol., 3:2156–2165.
Soto D. et al., 1992, PCR Methods and Applications, 2:96–98.
Stone B. B. et al., 1996, Mol. and Cell. Probes, 10:359–370.
Sugimura T. et al., 1992, Science (Washington D.C.), 258:603–607.
Takahashi, K., Kudo, J., Ishibashi, H., Hirata, Y. and Niho, Y. (1993). *Hepatology,* 17, 794–799.
Takahashi, S., Shan, A. L., Ritland, S. R., Delacey, K. A., Bostwick, D. J., Lieber, M. M., Thibodeau, N. and Jenkins, R. B. (1995). *Cancer Res,* 55, 4114–4119.
Takita, J., Hayashi, Y., Khono, T., Shiseki, M., Yamaguchi, N., Hanada, R., Yamamoto, K. and Yokota, J. (1995). *Oncogene,* 11, 1829–1834.
Tsuda, H., Zhang, W., Shimosato, Y., Yokota, J., Terada, M., Sugimura, T., Miyamura, T. and Hirohashi, S. (1990). *Proc. Natl. Acad. Sci. USA,* 87, 6791–6794.
Urdea M. S. et al., 1991, Nucleic Acids Symp. Ser., 24:197–200.
Vignal, A., Gyapay, G., Hazan, J., Nguyen, S., Dupraz, C., Cheron, N., Becuwe, N., Tranchant, M. and Weissenbach, J. (1993). *Methods in Molecular Genetics,* Vol. 1. Academic Press, Inc.
Wahl G. M. et al., 1987, Proc. Natl. Acad. Sci. USA, 84:2160–2164.
Walker G. T. et al., 1992, Nucleic Acids Res., 20:1691–1696.
Walker G. T. et al., 1992, Proc. Natl. Acad. Sci. USA, 89:392–396.
Wang J. et al., 1990, Nature, 343:555–557.
Wang, H. P. and Rogler, C. E. (1988). *Cytogenet. Cell Genet.,* 48, 72–78.
Wang, J., Chenivesse, X., Henglein, B. and Brechot, C. (1990). *Nature (London),* 343, 555–557.
Weinberg, R. A. (1991). *Science,* 254, 1138–1146.
White M. B. et al., 1992, Genomics, 12:301–306.
Wogan G. N., 1992, Cancer Res., 52:2114–2118.
Wooster, R., Bignell, G., Lancaster, J., Swift, S., Seal, S.et al (1995). *Nature,* 378, 789–792.
Yap E. P. H. et al., 1993, Nucleic Acids Res., 21(17):4155.
Yeh, S. H., Chen, P. J., Chen, H. L., Wang, C. C. and Chen, D. S. (1994). *Cancer Res.,* 54, 4188–4192.
Zhang, X., Xu, H. J., Murakami, Y., Sachse, R., Yashima, K., Hirohashi, S., Hu, S. X., Benedict, W. F. and Sekiya, T. (1994). *Cancer Res.,* 54, 4177–4182.

What is claimed is:

1. A composition for the predictive diagnosis of an hepatocellular carcinoma in a patient consisting essentially of a first isolated polynucleotide primer or a pair of isolated polynucleotide primers capable of specifically detecting or amplifying a first microsatellite DNA marker and a second isolated polynucleotide primer or a pair of isolated polynucleotide primers capable of specifically detecting or amplifying a second microsatellite DNA marker, wherein:
   said first microsatellite DNA marker is selected from the group consisting of D1S235, D1S238, D2S125, D2S336, D7S495, D8S263, D9S164, D9S273, and D17S928; and in that:
   said second microsatellite DNA marker is selected from the group consisting of D1S199, D1S235, D1S238, D1S247, D1S255, D1S436, D1S478, D1S2644, D1S2828, D2S125, D2S336, D4S400, D4S426, D4S1564, D4S1572, D4S1616, D4S2937, D4S2945, D6S305, D7S493, D7S495, D8S262, D8S263, D8S264, D8S277, D8S518, D8S1469, D8S1721, D8S1731, D8S1742, D8S1752, D8S1819, D9S164, D9S273, D13S284, D14S81, D14S265, D14S280, D14S292, D14S995, D16S402, D16S422, D16S505, D16S511, D16S3098, D17S786 and D17S928; and
   providing that said first and said second microsatellite DNA markers are not the same.

2. A composition according to claim 1, wherein said first microsatellite DNA marker is selected from the group consisting of D1S238, D1S235, D2S336, D2S125, D7S495, D9S164 and D17S928.

3. A composition according to claim 1, wherein said second microsatellite DNA marker is selected from the group consisting of D4S426, D6S305, D7S493, D8S277, D13S284 and D17S786.

4. A composition according to claim 1, wherein said second microsatellite DNA marker is selected from the group consisting of D8S1742, D8S1469, D8S1731, D8S1752, D1S2644, D1S199, D1S478, D1S2828, D1S247, D1S255, D14S280, D14S995, D14S81, D14S265, D14S292, D16S3098, D16S505, D16S511, D16S422 and D16S402.

5. A composition for the predictive diagnosis of an hepatocellular carcinoma in a patient wherein said composition comprises:
   a) an isolated polynucleotide primer or a pair of isolated polynucleotide primers capable of specifically detecting or amplifying the D14S81 microsatellite DNA marker;
   b) an isolated polynucleotide primer or a pair of isolated polynucleotide primers capable of specifically detecting or amplifying a microsatellite DNA marker selected from the group consisting of D8S264, D8S262, D8S518, D8S1742, D8S277, D8S1819, D8S1721, D8S1731 and D8S1752;
   c) an isolated polynucleotide primer or a pair of isolated polynucleotide primers capable of specifically detecting or amplifying a microsatellite DNA marker selected from the group consisting of D1S436, D1S2644, D1S199, D1S478, D1S2828, D1S247 and D1S255;
   d) an isolated polynucleotide primer or a pair of isolated polynucleotide primers capable of specifically detecting or amplifying a microsatellite DNA marker selected from the group consisting of D16S3098, D16S505, D16S511, D16S422 and D16S402; and
   e) an isolated polynucleotide primer or a pair of isolated polynucleotide primers capable of specifically detecting or amplifying a microsatellite DNA marker selected from the group consisting of D4S400, D4S1572, D4S1564, D4S2945, D4S1616 and D4S2937.

* * * * *